(12) United States Patent
Cima et al.

(10) Patent No.: US 11,065,426 B2
(45) Date of Patent: *Jul. 20, 2021

(54) IMPLANTABLE DEVICE WITH INTRAVESICAL TOLERABILITY AND METHODS OF TREATMENT

(71) Applicant: TARIS Biomedical LLC, Lexington, MA (US)

(72) Inventors: Michael J. Cima, Winchester, MA (US); Heejin Lee, Arlington, MA (US)

(73) Assignee: TARIS Biomedical LLC, Lexington, MA (US)

( * ) Notice: Subject to any disclaimer, the term of this patent is extended or adjusted under 35 U.S.C. 154(b) by 1365 days.

This patent is subject to a terminal disclaimer.

(21) Appl. No.: 14/224,256

(22) Filed: Mar. 25, 2014

(65) Prior Publication Data

US 2014/0221981 A1 Aug. 7, 2014

Related U.S. Application Data

(63) Continuation of application No. 12/972,364, filed on Dec. 17, 2010, now Pat. No. 8,679,094.
(Continued)

(51) Int. Cl.
*A61M 31/00* (2006.01)
*A61K 31/167* (2006.01)
(Continued)

(52) U.S. Cl.
CPC ......... *A61M 31/002* (2013.01); *A61K 9/0034* (2013.01); *A61K 9/2072* (2013.01);
(Continued)

(58) Field of Classification Search
CPC ... A61M 31/002; A61M 31/00; A61K 9/0034; A61F 2/042
See application file for complete search history.

(56) References Cited

U.S. PATENT DOCUMENTS

| 3,935,860 A | 2/1976 | Hoff |
| 4,016,251 A | 4/1977 | Higuchi et al. |

(Continued)

FOREIGN PATENT DOCUMENTS

| EP | 0572932 A2 | 5/1993 |
| WO | 20030098882 A2 | 2/2003 |

(Continued)

OTHER PUBLICATIONS

Tyagi, et al., Local Drug Delivery to Bladder Using Technology Innovations, Urological Clinics of North America, 2006, 519-530, vol. 33, Elsevier Inc.

(Continued)

*Primary Examiner* — Bradley J Osinski
(74) *Attorney, Agent, or Firm* — Eversheds Sutherland (US) LLP

(57) ABSTRACT

Intravesical devices are provided that are wholly deployable within the bladder of a patient in need of treatment and are well tolerated by the patient. The device may include an elastic body having a retention shape having (i) dimensions that provide intravesical mobility and that prevent voiding of the medical device through the urethra, and (ii) dimensions, buoyancy, or both, that exclude the medical device from entering the orifices of the ureters. The elastic body may exert a maximum acting force less than 1N when compressed to a shape with a maximum dimension in any dimension of 3 cm. The device may include a drug for controlled release within the bladder, for treatment of the bladder or a regional tissue. Methods of treatment are also provided that include selecting a patient in need of treatment in the bladder where tolerability of the treatment is a primary concern.

39 Claims, 6 Drawing Sheets

Related U.S. Application Data

(60) Provisional application No. 61/325,713, filed on Apr. 19, 2010, provisional application No. 61/287,649, filed on Dec. 17, 2009.

(51) Int. Cl.
*A61K 9/00* (2006.01)
*A61L 31/18* (2006.01)
*A61K 9/20* (2006.01)
*A61K 31/00* (2006.01)
*A61L 31/16* (2006.01)
*A61F 2/04* (2013.01)

(52) U.S. Cl.
CPC ............ *A61K 31/00* (2013.01); *A61K 31/167* (2013.01); *A61L 31/16* (2013.01); *A61L 31/18* (2013.01); *A61M 31/00* (2013.01); *A61F 2/042* (2013.01); *A61L 2300/402* (2013.01); *A61L 2300/602* (2013.01); *A61L 2430/22* (2013.01)

(56) References Cited

U.S. PATENT DOCUMENTS

| | | |
|---|---|---|
| 4,871,542 A | 10/1989 | Vilhardt |
| 4,968,507 A | 11/1990 | Zentner et al. |
| 5,516,522 A | 5/1996 | Peyman et al. |
| 5,795,591 A | 8/1998 | Lee et al. |
| 6,139,535 A | 10/2000 | Greelis et al. |
| 6,183,461 B1 | 2/2001 | Matsuura et al. |
| 6,207,180 B1 | 3/2001 | Ottoboni et al. |
| 6,293,923 B1 | 9/2001 | Yachia et al. |
| 6,398,718 B1* | 6/2002 | Yachia ................ A61B 5/0031 600/29 |
| 6,712,784 B2 | 3/2004 | Huang |
| 6,746,421 B2 | 6/2004 | Yachia et al. |
| 6,749,617 B1 | 6/2004 | Palasis et al. |
| 6,949,125 B2 | 9/2005 | Robertson |
| 6,976,950 B2 | 12/2005 | Connors et al. |
| 8,128,576 B2 | 3/2012 | Tracey et al. |
| 8,182,464 B2 | 5/2012 | Lee et al. |
| 2003/0118649 A1 | 6/2003 | Gao et al. |
| 2003/0229263 A1 | 12/2003 | Connors et al. |
| 2004/0022824 A1 | 2/2004 | Li et al. |
| 2004/0149294 A1 | 8/2004 | Gianchandani et al. |
| 2004/0260272 A1* | 12/2004 | Friedman et al. ......... 604/890.1 |
| 2005/0177067 A1 | 8/2005 | Tracey et al. |
| 2005/0228482 A1 | 10/2005 | Herzog et al. |
| 2006/0105010 A1* | 5/2006 | Rahe ........................ A61F 2/02 424/422 |
| 2006/0264912 A1 | 11/2006 | McIntyre et al. |
| 2007/0202151 A1* | 8/2007 | Lee ...................... A61K 9/0034 424/426 |
| 2007/0255222 A1 | 11/2007 | Li et al. |
| 2009/0149833 A1* | 6/2009 | Cima .................. A61K 9/0024 604/517 |
| 2009/0247992 A1 | 10/2009 | Shalon et al. |
| 2010/0003297 A1 | 1/2010 | Tobias et al. |
| 2010/0076261 A1 | 3/2010 | Neeman et al. |
| 2010/0330149 A1* | 12/2010 | Daniel ................. A61K 9/0034 424/430 |
| 2010/0331770 A1 | 12/2010 | Lee et al. |
| 2011/0060309 A1 | 3/2011 | Lee et al. |

FOREIGN PATENT DOCUMENTS

| | | |
|---|---|---|
| WO | 2004037318 A2 | 5/2004 |
| WO | 2006121969 A1 | 11/2006 |

OTHER PUBLICATIONS

Dis R&D Profile, "Oxybutynin Intravesical—Situs, I-Oxy," Drugs R&D 2002; 3 (2): 82-83.

Appell, Rodney A. et al., "339—A Novel Intravesical Device for Optimal Drug Delivery," The Journal of Urology, vol. 163, No. 4, Supplement, Sunday, Apr. 30, p. 77.

* cited by examiner

IMPLANTABLE DEVICE WITH INTRAVESICAL TOLERABILITY AND METHODS OF TREATMENT

CROSS-REFERENCE TO RELATED APPLICATIONS

This application is a continuation of U.S. application Ser. No. 12/972,364, filed Dec. 17, 2010, now U.S. Pat. No. 8,679,094, issued Mar. 25, 2014, which claims priority to U.S. Provisional Application No. 61/287,649, filed Dec. 17, 2009, and U.S. Provisional Application No. 61/325,713, filed Apr. 19, 2010, each of which is incorporated by reference herein in its entirety.

BACKGROUND

This disclosure is generally in the field of implantable medical devices and methods, more particularly in the field of drug delivery devices deployable within the bladder.

Systemic methods of drug delivery may produce undesirable side effects and may result in the distribution and metabolization of the drug by physiological processes, ultimately reducing the quantity of drug to reach the desired site. A variety of devices and methods have been developed to deliver drug in a more targeted manner, e.g., locally or regionally, which may address many of the problems associated with systemic drug delivery. Local delivery of drug to some tissue sites, however, has room for improvement, particularly with respect to extended drug delivery with minimally invasive devices and method and with minimum patient discomfort.

Interstitial cystitis (IC), painful bladder syndrome (PBS), and chronic prostatitis/chronic pelvic pain syndrome (CP/CPPS) are chronic painful disorders that are often treated by delivering a lidocaine solution to the bladder via instillation. To achieve sustained relief, repeated instillations may be required, such as three times per week for two weeks. The frequency of such instillations may be undesirable, as each instillation entails the inconvenience, discomfort, and risk of infection associated with urinary catheterization. Similarly, intermittent catheterization may be used to deliver drugs to the bladder that ease symptoms of neurogenic bladder. However, catheterization carries the drawbacks described above, among others. Thus, treatments could benefit from an intravesical drug delivery device that is implanted in the bladder.

Other therapies also could benefit from improved intravesical drug delivery devices, particularly where local delivery of a drug to the bladder is preferred or necessary—such as when the side effects associated with systemic delivery of the drug are intolerable and/or when bioavailability from oral administration is too low.

Situs Corporation developed an intravesical drug delivery system (UROS infuser device) for the delivery of pharmaceutical solutions of drugs, such as oxybutynin (for the treatment of overactive bladder) and mitomycin C (for the treatment of bladder cancer). The UROS infuser device and methods of implanting the device are disclosed in U.S. Pat. Nos. 6,171,298, 6,183,461, and 6,139,535. One problem with such devices is that the device is relatively large because a relatively large volume device is required to contain both a sufficient amount of the drug solution and the inlet/outlet valve mechanism.

Previous attempts at bladder drug delivery devices show that tolerability of the device in the bladder is a patient concern and a technical hurdle. For certain conditions or diseases, such as where the disease or condition is potentially fatal if left untreated (e.g., cancer), tolerability may be a secondary consideration. However, for other indications, tolerability may be a primary consideration. Unfortunately, known bladder devices, due perhaps to their large size or other mechanical characteristics, have not been well tolerated by patients and would be unsuitable in indications where tolerability is a primary concern, particularly where the treatment process would advisably require deployment and drug release over an extended period.

A need therefore exists for an intravesical drug delivery device that is sufficiently small to avoid unnecessary discomfort and pain during and following deployment of the device into patients, that can reduce the number of surgical or interventional procedures required for implantation and delivery of drug over the treatment period—e.g., that provides controlled delivery over an extended period, and that can carry an effective amount of drug for the extended period in a sufficiently small payload volume. In bladder applications, the device desirably should be retained in the bladder and not excreted before the drug payload can be at least substantially released, even when the drug needs to be delivered over a period of several days or weeks. In general, better devices are needed for controlled delivery of drug to the bladder. Desirably, the implantable device should be easy to deliver into (and if necessary, remove from) the bladder with reduced pain or discomfort to the patient.

SUMMARY

Improved intravesical devices and methods of treatment are provided. In one aspect, a medical device is provided that is wholly deployable within the bladder of a patient, such as a human, in need of treatment and is well tolerated by the patient. In one embodiment, the device includes an elastic body having a retention shape having (i) dimensions that provide intravesical mobility and that prevent voiding of the medical device through the urethra, and (ii) dimensions, buoyancy, or both, that exclude the medical device from entering the orifices of the ureters. The elastic body may exert a maximum acting force less than 1 N when compressed to a shape with a maximum dimension in any dimension of 3 cm, or 1.5 cm. The device in the retention shape and uncompressed may have a maximum dimension in any direction that is less than 10 cm, such as less than 5 cm. The device in a dry state may have a density of about 1.5 g/mL or less, such as about 0.5 g/mL to about 1.3 g/mL. In one embodiment, the elastic body houses or otherwise includes a drug for controlled release within the bladder. In a preferred embodiment, the drug is part of a formulation that is in the form of a plurality of compressed tablets housed in the elastic body.

In one aspect, a drug delivery device is provided which is wholly deployable within the bladder of a human patient and well tolerated by the patient. The device includes an elastic body housing a solid drug formulation, wherein the device is deformable between a deployment shape for passage of the device through the urethra and a retention shape for preventing voiding of the device through the urethra, the retention shape having a maximum dimension in any dimension of 5 cm when in an uncompressed state and wherein the device exerts a maximum acting force less than 1 N when the retention shape is compressed to a shape having a maximum dimension in any dimension of 3 cm. The drug formulation may comprise lidocaine, another anesthetic, or another drug.

In another aspect, a method of treatment of a human patient is provided, which method includes (i) selecting a patient in need of treatment in the bladder where tolerability of the treatment is a primary concern; (ii) deploying a drug delivery device into the patient's bladder through the patient's urethra; and (iii) releasing a drug into the bladder from the deployed drug delivery device over a treatment period. In one embodiment, the patient cannot feel the deployed device within his or her bladder during at least a majority of the treatment period. The selected patient may be indicated to be in need of treatment for overactive bladder; painful bladder syndrome; interstitial cystitis; an infection of the bladder, prostate, or urethra; neurogenic bladder; prostatitis or urethritis; or perioperative or postoperative pain associated with a urological surgery on the patient.

In another aspect, a method is provided for treating a genitourinary tissue site in a patient. In one embodiment, the method includes deploying a drug delivery device into the bladder of the patient; and releasing a drug from the drug delivery device into the bladder in an amount and at a rate to administer a therapeutically effective amount of the drug to at least one genitourinary tissue site other than the bladder. For example, the genitourinary tissue sites may be the urethra, ureter, kidneys, penis, testes, prostate, seminal vesicles, ejaculatory ducts, vas deferens, vagina, uterus, ovaries, fallopian tubes, or a combination thereof. The method may include selecting a patient in need of treatment where tolerability of the drug delivery device to be deployed in the bladder is a primary concern. The drug may include lidocaine or another anesthetic agent. The selected patient may be indicated to be in need of treatment for perioperative or postoperative pain associated with a urological surgery on the patient.

DETAILED DESCRIPTION

Figure 1:
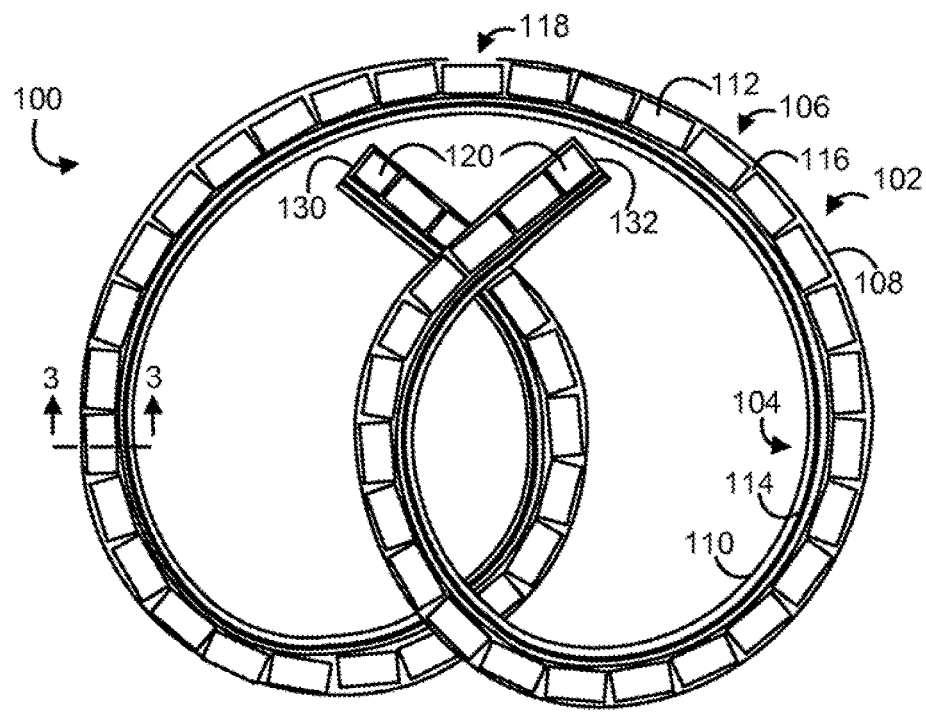
FIG. 1 is a plan view of an embodiment of a drug delivery device.

Implantable devices are provided that can be implanted in a lumen or body cavity of a patient, such as the bladder or another genitourinary site, for release of one or more drugs over an extended period. It was unexpectedly and beneficially discovered that an intravesical device having certain attributes can when wholly deployed within the bladder of a patient be well tolerated by the patient. In fact surprisingly in some embodiments, the presence of the device in the bladder may be unnoticeable to the patient. The device has a combination of characteristics that facilitate both its functionality and tolerability. These characteristics, as detailed below, include the size and shape of the device in combination with its compressibility and in some cases its the density, among others, which determine how mobile the device is within the bladder and to what degree the device contacts the trigone region or bladder wall.

Generally, it is believed that the more mobile the device is, then the more tolerable the device is. In addition, the dimensions are large enough to prevent voiding of the medical device through the urethra and to prevent the medical device from entering the orifices of the ureters. Another characteristic is the density of the device, which determines, for example, whether the device will float in urine in the bladder, which also impacts how the device feels in the patient's bladder. Still another characteristic that is believed to bear on tolerability is the stiffness, or spring constant, of the device when in its deployed shape. The device, in a preferred embodiment, has a size, shape, and/or minimum spring constant sufficient to prevent voiding of the medical device from the bladder. For example, it should not be so pliable (i.e., have such a low spring constant) that hydrodynamic forces during urination are effective to cause the device to bend or reshape into a low-profile configuration that would permit the device to pass from the bladder during urination. In addition, the device should not be so stiff and unpliable that it causes discomfort or pain to the patient when the device contacts the bladder wall.

Another aspect of the tolerability discovery is that certain therapies therefore advantageously become suitable for human patient populations for whom tolerability of the device in the bladder is primary concern.

The implantable device is designed for deployment into and retention within a portion of the body, such as the bladder. The device may be flexible so that the device can be deformed for insertion, yet once implanted the device may resist excretion in response to the forces of urination or other forces. In particular embodiments, an implantable drug delivery device is loaded with one or more drugs in the form of a number of solid drug units, such as tablets or pellets. Advantageously, the drug loaded device in a preferred embodiment is flexible or deformable despite being loaded with solid drug, as each drug unit may be permitted to move with reference to adjacent drug units.

In particular embodiments, the drug delivery device is small, such as small enough to be inserted through a deployment instrument extending through the urethra into the bladder. Such a device may be loaded with solid drug tablets that are substantially smaller than conventional drug tablets, and unlike conventional tablets the drug tablets also may constitute mostly drug and little or no excipients, so that the drug tablets contain a large amount of drug considering the tablet size. In particular embodiments, the drug delivery device may deliver lidocaine or another cocaine analogue locally to the bladder over a relatively extended period for the treatment of a condition such as IC/PBS, neurogenic bladder, or pain such as post-operative pain.

The device may be implanted non-surgically and may deliver drug long after the implantation procedure has ended. For example, the device may be deployed through a deployment instrument, such as a catheter or cystoscope, positioned in a natural lumen of the body, such as the urethra, into a body cavity, such as the bladder.

The drug delivery device may deliver drug locally and/or regionally to one or more genitourinary sites within the body. The device may be wholly implanted in the bladder to deliver drug locally to the bladder and regionally to nearby sites. Thus, drug delivery to one genitourinary sites can be achieved using a drug delivery device implanted in another genitourinary site.

When implanted in the bladder, the device overcomes many deficiencies of conventional treatments, such as delivery via instillation, which must be repeated; delivery via conventional devices, which must be re-filled once implanted; delivery via catheters, which provide a path for bacteria to migrate into the bladder, and systemic delivery, with its associated risk of side effects and reduced drug delivery to the target site. On the contrary, the present device can be implanted once and can release drug over an extended period without surgery or frequent interventions, reducing the opportunity for infection and side effects, increasing the amount of drug delivered locally or regionally to the bladder, and improving the quality of life of the patient during the treatment process. Thereafter, the device may be removed. Alternatively, the device may be partially or substantially bioerodible so that an invasive retrieval procedure can be avoided.

The devices and methods disclosed herein may be adapted for use in humans, whether male or female, adult or child, or for use in animals, such as for veterinary or livestock applications.

The devices and methods disclosed herein build upon those described in the following U.S. patent applications, which are incorporated by reference herein: U.S. application Ser. No. 11/463,956, filed Aug. 11, 2006; U.S. application Ser. No. 12/333,182, filed Dec. 11, 2008; U.S. application Ser. No. 12/538,580, filed Aug. 10, 2009; U.S. application Ser. No. 12/825,215, filed Jun. 28, 2010; U.S. application Ser. No. 12/825,238, filed Jun. 28, 2010; U.S. application Ser. No. 12/851,494, filed Aug. 5, 2010; U.S. application Ser. No. 12/870,261, filed Aug. 27, 2010; PCT US 2010/48266, filed Sep. 9, 2010; U.S. application Ser. No. 12/879,638, filed Sep. 10, 2010; U.S. application Ser. No. 12/963,621, filed Dec. 8, 2010; U.S. Provisional Application No. 61/311,103, filed Mar. 5, 2010; U.S. Provisional Application No. 61/370,902, filed Aug. 5, 2010; U.S. Provisional Application No. 61/371,139, filed Aug. 5, 2010; U.S. Provisional Application No. 61/390,495, filed Oct. 6, 2010; U.S. Provisional Application No. 61/390,549, filed Oct. 6, 2010; and U.S. Provisional Application No. 61/405,379, filed Oct. 21, 2010.

I. The Implantable Drug Delivery Device

An embodiment of a drug delivery device 100 is illustrated in FIG. 1. The device 100 includes a drug reservoir portion 102 and a retention frame portion 104. In FIG. 1, the device 100 is shown in a relatively expanded shape suited for retention in the body, and in FIG. 2 the device 100 is shown in a relatively lower-profile shape for deployment through the channel 200 of a deployment instrument, such as a cystoscope or other catheter. Following deployment into the body, the device 100 may assume the relatively expanded shape to retain the drug delivery device in the body cavity or lumen.

For the purposes of this disclosure, terms such as "relatively expanded shape", "relatively higher-profile shape", or "retention shape" generally denote any shape suited for retaining the device in the intended implantation location, including but not limited to the pretzel shape shown in FIG. 1 that is suited for retaining the device in the bladder. Similarly, terms such as "relatively lower-profile shape" or "deployment shape" generally denote any shape suited for deploying the drug delivery device into the body, including the linear or elongated shape shown in FIG. 2 that is suited for deploying the device through the working channel of catheter, cystoscope, or other deployment instrument positioned in a lumen of the body, such as the urethra. In embodiments, the drug delivery device may naturally assume the relatively expanded shape and may be deformed, either manually or with the aid of an external apparatus, into the relatively lower-profile shape for insertion into the body. Once deployed the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. For example, the drug reservoir portion 102 may be attached to the retention frame portion 104 at discrete points but otherwise may be separate or spaced apart from the retention frame portion 104.

In particular, the drug delivery device 100 includes an elastic or flexible device body 106 that defines a drug reservoir lumen 108 and a retention frame lumen 110. The drug reservoir lumen 108 is designed to house a drug formulation, such as a number of solid drug tablets 112, to form the drug reservoir portion 102. The retention frame lumen 110 is designed to house a retention frame 114 to form the retention frame portion 104. The illustrated lumens 108, 110 are discrete from each other, although other configurations are possible.

Figure 3:
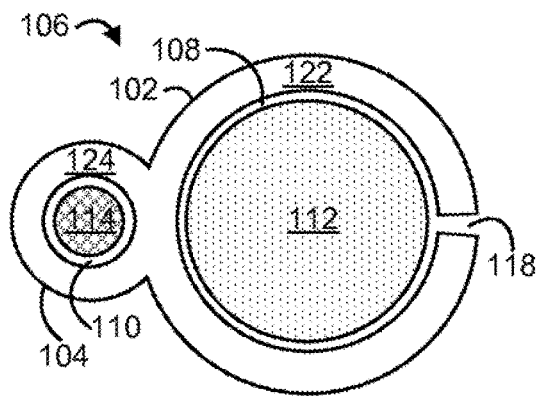
FIG. 3 is a cross-sectional view of the drug delivery device shown in FIG. 1, taken along line 3-3 in FIG. 1.

As shown in the cross-sectional view of FIG. 3, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The device body 106 may be formed integrally, such as via molding or extrusion, although separate construction and assembly of the tubes 122, 124 is possible. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. Further, the two walls 122, 124 are attached along the entire length of the device in the illustrated embodiment, although intermittent attachment can be employed. In one example, the wall 122 of the drug reservoir lumen 108 has an inner diameter of about 1.5 mm and an outer diameter of about 1.9 mm, while the wall 124 of the retention frame lumen 110 has an inner diameter of about 0.5 min and an outer diameter of about 0.9 mm. The cross-sectional area of the entire body of the device 106 may be about 0.035 cm$^2$ or less.

An aperture 118 may be formed through the wall 124 that defines the drug reservoir lumen 108. The aperture 118 may provide a passageway for releasing drug from the drug reservoir lumen 108 as further described below. However, the aperture 118 may be omitted in some embodiments.

As shown in FIG. 1, the drug reservoir lumen 108 is loaded with a number of drug units 112 in a serial arrangement. For example, between about 10 and about 100 drug units 112 may be loaded, such as between about 30 and about 70 drug units 112, or more particularly between about 50 and 60 drug units 112. However, any number of drug units may be used. The drug reservoir lumen 108 includes an entry 130 and an exit 132, which are shown as relatively circular openings at opposite ends of the drug reservoir lumen 108. The entry 130 provides ingress for the drug units 112 to be placed into the drug reservoir lumen 108 during device loading and assembly, such as by a flow of pressurized gas, in which case the exit 132 provides egress for the flow of pressurized gas to escape from the drug reservoir lumen 108. Once the drug units 112 are loaded, at least two end plugs 120 block the entry 130 and exit 132. The end plugs 120 may be cylindrical plugs inserted into the entry 130 and the exit 132, each having a slightly larger outer diameter than an inner diameter of the drug reservoir lumen 108 so that the plugs substantially enclose the entry 130 and exit 132 and are snugly retained in position. In some cases, a number of end plugs 120 can be positioned in the entry 130 or the exit 132. The end plugs 120 may be silicone plugs. The end plugs 120 also may be omitted, in which case the entry 130 and exit 132 may be closed with a material, such as adhesive, that is placed in the drug reservoir lumen 108 in workable form and cures therein.

In some embodiments, the drug tablets 112 may not fill the entire drug reservoir lumen 108. In such embodiments, a filling material may be used to fill the remainder of the drug reservoir lumen 108. For example, the drug tablets 112 may be loaded in a central portion of the drug reservoir lumen 108 and the filling material may be loaded in the remaining end portions of the drug reservoir lumen 108. The filling material may be inserted into the end portions of the drug reservoir lumen 108 after the lumen is filled with the drug tablets 112. The filling material may be a polymeric material. The polymeric material may be placed in the drug reservoir lumen 108 in workable form and may cure therein. Suitable polymeric materials may cure at room temperature or in response to an external stimulus, such as heat. In some cases, the filling material may enclose the entry 130 and exit 132, in which case the end plugs 120 may or may not be provided. The filling material also may be a number of end plugs 120 inserted into the end portions of the drug reservoir lumen 108.

Once the drug units 112 are loaded, interstices 116 or breaks may be formed between adjacent drug units 112. The interstices or breaks 116 may serve as reliefs that accommodate deformation or movement of the device 100, while permitting the individual drug units 112 to retain their solid form during storage and deployment. Thus, the drug delivery device 100 may be relatively flexible or deformable despite being loaded with a solid drug, as each drug unit 112 may be permitted to move with reference to adjacent drug units 112. Along the length of the device drug reservoir lumen 108, the drug units 112 may have the same composition or may vary in composition, and in some cases drug units 112 of different compositions may be in distinct reservoirs that are segregated, either axially or radially, along the length of the drug reservoir lumen 108.

The retention frame lumen 110 is loaded with the retention frame 114, which may be an elastic wire. The retention frame 110 may be configured to spontaneously return to a retention shape, such as the illustrated "pretzel" shape or another coiled shape. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once implanted, limiting or prevent accidental expulsion.

The material used to form the device body 106 may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases. The flexible material also allows the device body 106 to flex outward or circumferentially expand in response to a flow of pressurized gas through the drug reservoir lumen 108 during drug loading, as described below. The material used to form the device body 106 also may be water permeable or porous so that solubilizing fluid can enter the drug reservoir portion 102 to solubilize the drug units 112 once the device is implanted. For example, silicone or another biocompatible elastomeric material may be used.

In one embodiment in which the drug delivery device 100 is designed to be implanted in the bladder, the drug delivery device 100 is designed to be inserted into (and optionally retrieved from) the bladder through the urethra cystoscopically. Thus, the device may be sized and shaped to fit through a narrow tubular path of a deployment instrument, such as a catheter or cystoscope. Typically, a cystoscope for an adult human has an outer diameter of about 5 mm and a working channel having an inner diameter of about 2.4 mm to about 2.6 mm. In embodiments, a cystoscope having a working channel with a larger inner diameter, such as an inner diameter of 4 mm or more. Thus, the device may be relatively small in size. For example, when the device is elastically deformed to the relatively lower profile shape, the device for an adult patient may have a total outer diameter that is less than about 2.6 mm, such as between about 2.0 mm and about 2.4 mm. For pediatric patients, the dimensions of the device are anticipated to be smaller, e.g., proportional for example based on the anatomical size differences and/or on the drug dosage differences between the adult and pediatric patients. In addition to permitting insertion, the relatively small size of the device may also reduce patient discomfort and trauma to the bladder.

The overall configuration of the device facilitates ensuring the device is tolerable to the patient. It should be noted that the device may be tolerable to the patient while still being noticeable. The device is both tolerable and unnoticeable in preferred embodiments, while in other embodiments the device is tolerable but noticeable. A noticeable device may nonetheless be tolerable to the patient if the device is appropriately configured. For example, the device may be configured to reduce the likelihood of contacting the bladder wall and to reduce the pressure exerted by the device on the bladder wall when contact does occur. Bladder wall contact may cause bladder irritation that is uncomfortable for some patients and may be unbearable for sensitive patients, such as those suffering from IC/PBS. Thus, noticeability and tolerability may vary depending on differences in patient anatomy and perception of pain and discomfort. However, the overall configuration of the device may ensure tolerability for most patients.

To facilitate tolerability, the size of the device may be smaller than the bladder under most levels of bladder fullness. The size of the human bladder changes depending on whether the bladder is full or empty. For example, a typical bladder may hold about 500 mL when full and about 0 to 30 mL when empty, such as about 15 mL. The bladder is roughly spherical when full and varies in shape when empty or nearly empty, often assuming a roughly ellipsoidal shape when empty. A typical full bladder may have a diameter of about 10 cm to about 13 cm, while an empty bladder may have dimensions of about 3×4×2 cm, although the dimensions of the empty bladder may vary by as much as about 2 cm in any direction. For example, an empty bladder may have dimensions of about 5×5×1 cm. For the purposes of this disclosure, the diameter of the empty bladder is approximated to be about 3 cm, as the typical empty bladder may have a dimension of about 3 cm in at least one direction.

The fullness of the bladder also affects the intravesical pressure therein. The bladder pressure is sensed by nerves in the bladder wall so that a sense of bladder fullness and a desire to void are appropriately created. Typically, when the bladder contains between about 100 and 200 mL of urine, the pressure within the bladder is between about 8 and 15 cm $H_2O$ (about 0.79 to 1.47 kPa). At these pressures the first sensation of bladder fullness occurs, while lower pressures are mediated by nerves in the bladder wall so that no sensation of bladder fullness is created. As the bladder becomes full, a definite sensation of bladder fullness and an urge to urinate may be created. A full bladder may correspond to intravesical pressures of about 40 and 100 cm $H_2O$ (about 3.92 kPa to 9.8 kPa).

Figure 4:
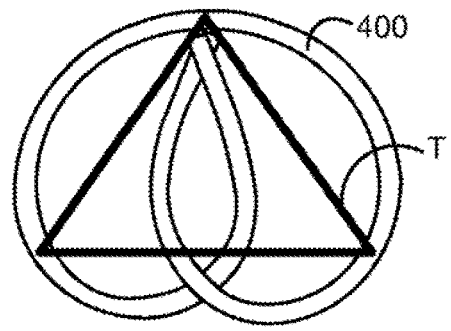
FIG. 4 is an illustration showing the size of an embodiment of a drug delivery device in comparison to an approximation of the bladder trigone region.

More particularly, the sensation of an urge to urinate is created within the bladder trigone region, which is an area of the bladder defined between the bladder neck and the ureteral orifices. The trigone can be approximated as a triangle having a top vertex that represents the bladder neck and two bottom vertices that represent the ureteral orifices. FIG. 4 shows an example triangle that approximates the trigone of an adult human male. In a human male, the distance from the bladder neck to one of the ureteral orifices is about 2.75 cm and the distance between the two ureteral orifices is about 3.27 cm. Thus, in FIG. 4, the distance from the top vertex to either of the bottom vertices is about 2.8 cm, while the distance between two bottom vertexes is 3.3 cm. The size of the trigone region may vary depending on the animal. In an adult female, for example, the distance between the two ureteral orifices is about 2.68 cm and the distance from a neck of the bladder to one of the ureteral orifices is about 2.27 cm. Smaller animals may have smaller trigone regions.

In view of these bladder characteristics, the device is configured to be tolerable within the bladder. In particular, the device is sized so that when the device is in the retention shape, the device is smaller than the bladder under most conditions of bladder fullness. A device that is smaller than the bladder under most conditions of bladder fullness may have reduced contact with the bladder wall, reducing irritation of the bladder wall and contact pressure that may be sensed as bladder fullness. However, when the device is in the retention shape, the device may have an overall size and shape that is selected so that when the device overlays the triangular approximation of the bladder trigone region, the device is larger than the triangular approximation. Such sizing limits the ability of the device to come to rest within the trigone region, which may be sensitive. Such sizing also limits the likelihood of a portion of the device entering or becoming trapped within the bladder neck and the ureteral orifices.

In some embodiments, the device in a retention shape may have dimensions in all directions that are less than 3 cm, so that when the bladder is empty, the device does not necessarily have to contact the bladder wall to fit within the bladder. In other embodiments, the device in the retention shape may have at least one dimension that is larger than 3 cm, so that a larger drug payload can be delivered. In such embodiments, the bladder wall may exert a pressure on the device that compresses the device in at least one direction so that it fits within the empty bladder, and the compressed device may exert a return pressure on the bladder wall. The return pressure may not exceed those pressures associated with a sensation of urgency of urination or bladder fullness, so that the device remains tolerable. Thus, the size and shape of the device may be selected so that when the device is compressed, the device exerts a pressure on the bladder wall that is less than about 9.8 kPa. In some embodiments, the size and shape of the device may be selected so that when the device is compressed, the device exerts a pressure on the bladder wall that is less than about 3.92 kPa. In particular embodiments, the size and shape of the device may be selected so that when the device is compressed, the device exerts a pressure on the bladder wall that is less than about 1.47 kPa and may be less than 0.79 kPa. These pressures can be achieved by varying the overall size of the device and the extent of its surface area. For example, the surface area of the device may be increased to decrease the pressure exerted against the bladder wall upon contact, although the overall cross-sectional area of the device may not be increased above a size that is deployable through the urethra.

It is possible to approximate the compression forces that the bladder may impose upon the device without the device in turn exposing the bladder to a pressure that exceeds the outer limit of 9.8 kPA, and more particularly 1.47 kPa. For example, a spherical device positioned in a spherical bladder is in contact with the bladder wall about its equator. Such a device can be approximated as exerting a pressure on the bladder wall of about 9.8 kPa when the bladder compresses the device with a total compressive force of about 7 N. Similarly, such a device can be approximated as exerting a pressure on the bladder wall of about 1.47 kPa when the bladder compresses the device with a total compressive force of about 1 N. Of course, devices with other, smaller surface areas can exert comparable pressures on the bladder while absorbing smaller compressive loads.

Thus, within the three-dimensional space occupied by the device in the retention shape, the maximum dimension of the device in any direction is less than 10 cm, the approximate diameter of the bladder when filled. In some embodiments, the maximum dimension of the device in any direction may be less than about 9 cm, such as about 8 cm, 7 cm, 6 cm, 5 cm, 4.5 cm, 4 cm, 3.5 cm, 3 cm, 2.5 or smaller. In particular embodiments, the maximum dimension of the device in any direction is less than about 7 cm, such as about 6 cm, 5 cm, 4.5 cm, 4 cm, 3.5 cm, 3 cm, 2.5 cm or smaller. In preferred embodiments, the maximum dimension of the device in any direction is less than about 6 cm, such as about 5 cm, 4.5 cm, 4 cm, 3.5 cm, 3 cm, 2.5 cm or smaller.

More particularly, the three-dimension space occupied by the device is defined by three perpendicular directions. Along one of these directions the device has its maximum dimension, and along the two other directions the device may have smaller dimensions. For example, the smaller dimensions in the two other directions may be less than about 4 cm, such as about 3.5 cm, 3 cm, or less. In a preferred embodiment, the device has a dimension in at least one of these directions that is less than 3 cm.

In some embodiments, the device may have a different dimension in at least two of the three directions, and in some cases in each of the three directions, so that the device is non-uniform in shape. Due to the non-uniform shape, the device may be able to achieve an orientation of reduced compression in the empty bladder, which also is non-uniform in shape. In other words, there may be a particular orientation for the device in the empty bladder that allows the device to exert less contact pressure against the bladder wall, making the device more tolerable for the patient.

The overall shape of the device may enable the device to reorient itself within the bladder to reduce its engagement or contact with the bladder wall. For example, the overall exterior shape of the device may be curved, and all or a majority of the exterior or exposed surfaces of the device may be substantially rounded. The device also may be substantially devoid of sharp edges, and is exterior surfaces may be formed from a material that experiences reduced frictional engagement with the bladder wall. Such a configuration may enable the device to reposition itself within the empty bladder so that the device applies lower contact pressures to the bladder wall. In other words, the device may slip or roll against the bladder wall into a lower energy position, meaning a position in which the device experiences less compression.

An example of a device that generally satisfies these characteristics is shown in FIG. 1, and examples of specific device configurations that satisfy these characteristics are described below with reference to Example 1 and Example 3. In particular, the illustrated device is generally planar in shape even though the device occupies three-dimensional space. Such a device may define a minor axis, about which the device is substantially symmetrical, and a major axis that is substantially perpendicular to the minor axis. The device may have a maximum dimension in the direction of the major axis that does not exceed about 6 cm, and in particular embodiments is less than 5 cm, such as about 4.5 cm, about 4 cm, about 3.5 cm, about 3 cm, or smaller. The device may have a maximum dimension in the direction of the minor axis that does not exceed about 4.5 cm, and in particular embodiments is less than 4 cm, such as about 3.5 cm, about 3 cm, or smaller. The device is curved about substantially its entire exterior perimeter in both a major cross-sectional plane and a minor cross-sectional plane. In other words, the overall exterior shape of the device is curved and the cross-sectional shape of the device is rounded. Thus, the device is substantially devoid of edges, except for edges on the two flat ends, which are completely protected within the interior of the device when the device lies in a plane. These characteristics enable the device to reorient itself into a position of reduced compression when in the empty bladder.

Such devices may exhibit certain behaviors when subjected to a compression test, wherein the device is compressed between two platens and the compressive load is captured as a function of the distance between the two platens. The distance between the platens corresponds to the dimension of the device in the direction of the compressive load. An example of such a compression test is described below with reference to Example 8, which shows that the devices described below in Example 1 and Example 3 can be compressed to a dimension of about 3 cm with an acting force of about 1 N or less. These devices were found to be tolerable within the bladder, as described below with reference to Examples 4, 5, 6, and 7. Thus, devices may be tolerable if compressible to a maximum dimension in any direction of about 3 cm with an acting force of about 1 N or less. In some cases, a device may be tolerable if the device can be compressed to a maximum dimension in any direction of about 3 cm with an acting force of about 0.5 N, about 0.2 N, about 0.1 N, about 0.01 N, or less. In such cases, it is thought that the pressure exerted on the bladder by the device may be below those ranges that result in an urgency of urination or a sensation of bladder fullness. By way of example, the device described below with reference to Example 1 was calculated to exert a pressure on the bladder wall of about 770 Pa when compressed to a maximum dimension of 3 cm, which may be below the pressure at which a sensation of fullness first emerges. Similarly, the device described below with reference to Example 3 was calculated to exert a pressure on the bladder wall of about 2.7 kPa when compressed to a maximum distance of 3 cm, which may be comfortably noticeable to the patient.

The device also may be small enough in the retention shape to permit intravesical mobility. In particular, the device when deployed may be small enough to move within the bladder, such as to move freely or unimpeded throughout the entire bladder under most conditions of bladder fullness, facilitating patient tolerance of the device. Free movement of the device also facilitates uniform drug delivery throughout the entire bladder, as opposed to a particular bladder location located near the release orifice. However, devices that otherwise move freely within the bladder may be impeded from moving freely when the bladder is completely empty, and yet the device may still be tolerable if sufficiently compressible as described above.

The device also may have a density that is selected to facilitate floatation. The device has a minimum density in a dry and unloaded state, meaning the device is not loaded with drug and fluid is not present in the device walls or lumens. Example 2 below describes a device in such an unloaded or placebo configuration. The density of the device increases when the device is loaded with drug. Example 1 and Example 3 below describe devices in such loaded or active configurations. The density of the device also increases when the device is in a wet state, meaning fluid is present in the device walls and lumens. The device enters the wet state upon implantation in the bladder, as the device becomes surrounded by urine. In use, the device may have a maximum density after implantation, when the device is loaded with the maximum drug payload and liquid displaces any air present in the walls and lumens. Subsequently, the density of the device may remain essentially the same or decrease as the drug is solubilized and released, and replaced by urine.

In general, the device in the dry and loaded state may have a density in the range of about 0.5 g/mL to about 1.5 g/mL, such as between about 0.7 g/mL to about 1.3 g/mL. In some embodiments, the device in the dry and loaded has a density that is less than the density of water, such as a density that is less than about 1 g/mL. Such densities facilitate buoyancy and movement in the bladder. Lighter or lower density materials may be integrated into the device as needed to compensate for any higher density drug or other payload in the device, thereby maintaining an overall density that facilitates buoyancy for tolerance purposes. In addition, air or another gas may be trapped in portions of the device to reduce the overall density. For example, the walls of retention frame lumen may be made impermeable to water such that an air pocket is formed in the retention frame lumen about the elastic wire. A coating or sheath may be applied to the walls, on either the inside or outside, to reduce the water permeability.

One example device may have a mass of about 0.40 grams or less and a density of about 0.7 g/mL or less when unloaded. The device may be loaded with a drug having a mass of about 275 mg or less. In such embodiments, the device when loaded may have a mass of about 0.675 grams or less and a density of about 1.1 g/mL or less. Such a device may be well tolerated in the bladder. Devices of smaller masses and densities would likewise be well tolerated.

The exact configuration and shape of the intravesical drug delivery device may be selected depending upon a variety of factors including the specific site of deployment/implantation, route of implantation, drug, dosage regimen, and therapeutic application of the device. The design of the device may minimize the patient's pain and discomfort, while locally delivering a therapeutically effective dose of the drug to a tissue site (e.g., urothelial tissue) in a patient.

The implantable drug delivery device can be made to be completely or partially bioerodible so that no explanation, or retrieval, of the device is required following release of the drug formulation. As used herein, the term "bioerodible" means that the device, or part thereof, degrades in vivo by dissolution, enzymatic hydrolysis, erosion, resorption, or a combination thereof. In one embodiment, this degradation occurs at a time that does not interfere with the intended kinetics of release of the drug from the device. For example, substantial erosion of the device may not occur until after the drug formulation is substantially or completely released. In another embodiment, the device is erodible and the release of the drug formulation is controlled at least in part by the degradation or erosion characteristics of the erodible device body.

Alternatively, the implantable drug delivery device may be at least partially non-bioerodible. In some embodiments, the device is formed from materials suited for urological applications, such as medical grade silicone, natural latex, PTFE, ePTFE, PLGA, PGS, stainless steel, nitinol, elgiloy (non ferro magnetic metal alloy), polypropylene, polyethylene, polycarbonate, polyester, nylon, or combinations thereof. Following release of the drug formulation, the device and/or the retention frame may be removed substantially intact or in multiple pieces. In some embodiments, the device is partially bioerodible so that the device, upon partial erosion, breaks into non-erodible pieces small enough to be excreted from the bladder. Useful biocompatible erodible and non-erodible materials of construction are known in the art.

In a preferred embodiment, the drug delivery device is sterilized, such as after the device is manufactured/assembled and before the device is implanted. In some cases, the device may be sterilized after the device is packaged, such as by subjecting the package to gamma irradiation or ethylene oxide gas.

The Drug Reservoir Portion

In one embodiment, the drug reservoir portion of the device includes an elongated tube. An interior of the tube may define one or more drug reservoirs, and a drug formulation may be housed in the drug reservoir(s). In another embodiment, the drug reservoir portion is in a form other than a tube.

The release rate of the drug from the drug reservoir portion generally is controlled by the design of the combination of the device components, including but not limited to the materials, dimensions, surface area, and apertures of the drug reservoir portion, as well as the particular drug formulation and total mass of drug load, among others.

Figure 2:
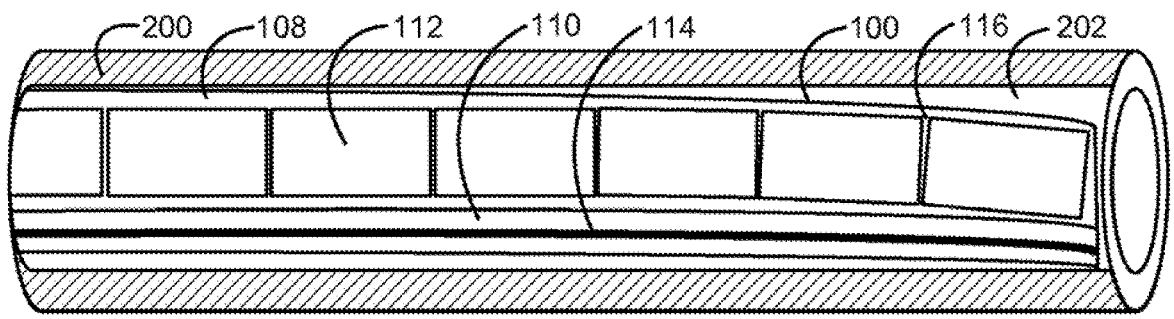
FIG. 2 is a plan view of the drug delivery device shown in FIG. 1, illustrating the drug delivery device inside a deployment instrument.

An example of such a drug reservoir portion is shown in FIGS. 1-3. As shown, the drug reservoir portion 102 may include a body formed from an elastomeric tube 122. The tube 122 defines a reservoir 108 that contains a number of drug tablets 112. Ends of the tube 122 may be sealed with sealing structures 120. At least one aperture 118 may be disposed in the tube 122. In cases in which an aperture 118 is provided, the aperture 118 may be closed by a degradable timing membrane, which may control the initiation of release of the drug formulation from the reservoir. In some cases, a sheath or coating may be positioned about at least a portion of the tube 122 to control or reduce the release rate, such as by reducing the osmotic surface area of the tube or by reducing diffusion through the tube wall. For simplicity, the degradable timing membranes and sheaths or coatings are not shown.

In one embodiment, the drug reservoir portion operates as an osmotic pump. In such embodiments, the tube may be formed from a water permeable material, such as a silicone, or tube may have a porous structure, or both. Following implantation, water or urine permeates through the wall of the tube, one or more apertures formed through the tube, or one or more passing pores formed through a porous tube. The water enters the reservoir, and is imbibed by the drug formulation. Solubilized drug is dispensed at a controlled rate out of the reservoir through the one or more apertures, driven by osmotic pressure in the reservoir. The delivery rate and overall performance of the osmotic pump is affected by device parameters, such as the surface area of the tube; the permeability to liquid of the material used to form the tube; the shape, size, number and placement of the apertures; and the drug formulation dissolution profile, among other factors. The delivery rate can be predicted from the physicochemical parameters defining the particular drug delivery system, according to well known principles, which are described, for example, in Theeuwes, *J. Pharm. Sci.*, 64(12): 1987-91 (1975). In some embodiments, the device may initially exhibit a zero-order release rate and subsequently may exhibit a reduced, non-zero-order release rate, in which case the overall drug release profile may be determined by the initial zero-order release rate and the total payload. Representative examples of osmotic pump designs, and equations for selecting such designs, are described in U.S. Patent Publication No. 2009/0149833.

In an alternative embodiment, the device may operate essentially by diffusion of the drug from the tube through (i) one or more discrete apertures formed in the wall of the tube, or passing pores formed in the wall of a porous tube, or (ii) through the wall of the tube itself, which may be permeable to the drug, or (iii) a combination thereof. In embodiments in which diffusion occurs through the wall, the apertures or passing pores may not be included. In still other embodiments, the device may operate by a combination of osmosis and diffusion.

The drug reservoir portion may be formed from an elastomeric material, which may permit elastically deforming the device for its insertion into a patient, e.g., during its deployment through deployment instrument such as a cystoscope or catheter. For example, the tube may be elastically deformed along with the retention frame for intravesical implantation, as described in further detail below.

In preferred embodiments, the drug reservoir portion is formed from a material that is both elastomeric and water permeable. One material that is both elastomeric and water permeable is silicone, although other biocompatible materials may be used.

The length, diameter, and thickness of the tube may be selected based on the volume of drug formulation to be contained, the desired rate of delivery of the drug from the tube, the intended site of implantation of the device within the body, the desired mechanical integrity for the device, the desired release rate or permeability to water and urine, the desired induction time before onset of initial release, and the desired method or route of insertion into the body, among others. The tube wall thickness may be determined based on the mechanical properties and water permeability of the tube material, as a tube wall that is too thin may not have sufficient mechanical integrity while a tube wall that is too thick may experience an undesirably long induction time for initial drug release from the device.

In one embodiment, the device body is non-resorbable. It may be formed of a medical grade silicone tubing, as known in the art. Other examples of suitable non-resorbable materials include synthetic polymers selected from poly(ethers), poly(acrylates), poly(methacrylates), poly(vinyl pyrolidones), poly(vinyl acetates), poly(urethanes), celluloses, cellulose acetates, poly(siloxanes), poly(ethylene), poly(tetrafluoroethylene) and other fluorinated polymers, poly(siloxanes), copolymers thereof, and combinations thereof.

In some embodiments, the device body is bioerodible. In one embodiment of a bioerodible device, the tube of the body is formed of a biodegradable or bioresorbable polymer. Examples of suitable such materials include synthetic polymers selected from poly(amides), poly(esters), poly(ester amides), poly(anhydrides), poly(orthoesters), polyphosphazenes, pseudo poly(amino acids), poly(glycerol-sebacate) (PGS), copolymers thereof, and mixtures thereof. In a preferred embodiment, the resorbable synthetic polymers are selected from poly(lactic acids), poly(glycolic acids), poly(lactic-co-glycolic acids), poly(caprolactones), and mixtures thereof. Other curable bioresorbable elastomers include poly(caprolactone) (PC) derivatives, amino alcohol-based poly(ester amides) (PEA) and poly (octane-diol citrate) (POC). PC-based polymers may require additional cross-linking agents such as lysine diisocyanate or 2,2-bis(ε-caprolacton-4-yl)propane to obtain elastomeric properties.

The tube of a drug reservoir portion tube may be substantially linear and in some cases may be substantially cylindrical with a circular cross-section, although square, triangle, hexagon, and other polygonal cross-sectional shapes can be used, among others.

The ends of the tube may be sealed to limit escape of the drug, such as with a sealing structure or other sealing means. The sealing structure may have any shape suited to plug or close the tube end, such as a cylinder 120 as shown in FIG. 1, a ball, a disk, or others. In some embodiments, the sealing structure may have a larger diameter than the inner diameter of the tube, such that the tube stretches to fit snugly about the sealing structure, closing the tube and retaining the sealing structure in place. The sealing structure may be formed from biocompatible material, including a metal such as stainless steel, a polymer such as silicone, a ceramic, sapphire, or adhesive, among others or combinations thereof. The material may be biodegradable or bioerodible. A medical grade silicone adhesive or other adhesive also may be loaded into the tube in a workable form and may then cure within the tube to seal the end.

In some embodiments, the tube may have multiple reservoirs. Each reservoir may be defined by a portion of the tube inner surface and at least one partition. The partition may be a partition structure or plug inserted into the tube, such as a cylinder, sphere, or disk, among others, in which case the partition structure may have a larger cross-section than the tube, securing the partition structure in place and segregating adjacent reservoirs. For example, the cylindrical plug 120 of FIG. 1 that closes the tube end may instead serve as a partition structure to segregate two reservoirs positioned adjacent to each other along the length of the tube. The partition may be non-porous or semi-porous, non-resorbable or resorbable and may be formed of a material described above with reference to the cylindrical plug 120. The partition also may be formed in the tube, such as by molding. For example, one or more webs may extend through the tube along its length to segregate axial reservoirs that extend along the length of the tube, as shown in Examples J through L of FIG. 6. The partition also may be a structure that joins two different tubes that serve as separate reservoirs, as shown in Examples M through O of FIG. 6.

The multiple reservoirs permit segregating two or more different drug formulations in different reservoirs, delivering a single drug from different reservoirs at different rates or times following implantation, or combinations thereof. For example, two different reservoirs may have different configurations, such as different materials, different permeabilities, different numbers or placements of apertures (or the absence of apertures), different timing membranes in the apertures, among others or combinations thereof. The two different reservoirs also may house the same or different drug formulations in the same or different forms (such as liquid, semi-solid, and solid), or combinations thereof. The two different reservoirs further may be configured to release drug via different release mechanisms, such as via osmosis through an aperture and by diffusion through a drug reservoir wall that may lack an aperture completely. Coatings or sheaths also may be provided along different portions of a single drug reservoir or along different drug reservoirs housing the same or different drug formulations. These embodiments can be combined and varied to achieve the desired release profile of the desired drug.

For example, the onset of release of two doses in different reservoirs can be staged by configuring the device accordingly, such as by using different materials for portions of the tube defining different reservoirs, by associating the aperture(s) of different reservoirs with different timing membranes, by placing drugs with different solubilities in the reservoirs, or by placing drugs with different forms in the reservoirs, such as a liquid form for immediate release and a solid form to be solubilized prior to release. Thus, the device may release some drug relatively quickly after implantation while other drug may experience an induction time before beginning release.

In one embodiment, the total volume of the reservoir (or combined reservoirs) is sufficient to contain all the drug needed for local delivery over the course of a single treatment, reducing the number of procedures needed to treat a particular condition.

Apertures

In some embodiments, the device includes one or more apertures or orifices for dispensing the drug, such as via osmosis, diffusion, or a combination thereof, among other. The apertures may be spaced along the tube to provide a passageway for release of the drug formulation. The apertures or orifices may be positioned through a sidewall or an end of the tube. The apertures may be in fluid communication with one or more reservoirs. An embodiment of an aperture 118 is shown on the drug reservoir portion in FIGS. 1 and 3.

The aperture may be located about a middle of the drug reservoir portion or adjacent to its exit, which may affect the ease of loading solid drug units into the drug reservoir portion as described below. The apertures may be positioned away from a portion of the tube that will be folded during insertion to limit tearing of degradable membranes on the apertures.

In embodiments in which the device includes a device body that defines both drug reservoir and retention frame lumens, such as the embodiment shown in FIG. 3, the aperture or apertures may have various positions on the wall of the drug reservoir lumen with reference to the wall of the retention frame lumen, as further described below.

The size, number, and placement of the apertures may be selected to provide a controlled rate of release of the drug. A device that operates primarily as an osmotic pump may have one or more apertures sized small enough to reduce diffusion of the drug through the aperture(s), yet large enough and spaced appropriately along the tube to reduce the buildup of hydrostatic pressure in the tube. Within these constraints, the size and number of apertures for a single device (or reservoir) can be varied to achieve a selected release rate. In exemplary embodiments, the diameter of the aperture is between about 20 μm and about 500 μm, such as between about 25 μm and about 300 μm, and more particularly between about 30 μm and about 200 μm. In one particular example, the aperture has a diameter between about 100 μm and about 200 μm, such as about 150 μm. In embodiments where the device operates primarily by diffusion, the apertures may be in this range or larger. A single device may have apertures of two or more different sizes. The aperture may be circular, although other shapes are possible and envisioned, with the shape typically depending on manufacturing considerations. Examples of processes for forming the apertures include mechanical punching, laser drilling, laser ablation, and molding. The aperture may slightly taper from an exterior to an interior of the tube, and the aperture may be created either before or after the drug is loaded into the tube. The aperture also may be formed in an orifice structure disposed in an end of the tube, such as a ruby or sapphire precision orifice structure from, for example, Bird Precision Orifices, Swiss Jewel Company.

In some embodiments, the drug reservoir portion may not have any apertures, in which case the drug may be released via a release mechanism other than osmosis, such as diffusion through the wall of the drug reservoir portion. Similarly, a drug reservoir portion having multiple discrete drug reservoirs may have apertures associated with all, some, or none of the drug reservoirs, in which cases release from the different drug reservoirs may occur via different release mechanisms.

Degradable Membranes

In one embodiment, a degradable membrane, i.e., a timing membrane, is disposed over or in the apertures (e.g., in register with the aperture) to control the onset of release of the drug formulation. The degradable membrane may be a coating over all or some of the outer surface of the tube or a discrete membrane above or within the aperture. Two or more degradable membranes also may be used to control release from one aperture. The membranes may be formed, for example, of a resorbable synthetic polymer (such as polyester, a poly(anhydride), or a polycaprolactone) or a resorbable biological material (such as cholesterol, other lipids and fats). Additional details are described in U.S. Publication No. 2009/0149833.

The Drug Formulation and Solid Drug Tablets

The drug formulation can include essentially any therapeutic, prophylactic, or diagnostic agent, such as one that would be useful to deliver locally to a body cavity or lumen or regionally about the body cavity or lumen. The drug formulation may consist only of the drug, or one or more pharmaceutically acceptable excipients may be included. The drug may be a biologic. The drug may be a metabolite. As used herein, the term "drug" with reference to any specific drug described herein includes its alternative forms, such as salt forms, free acid forms, free base forms, and hydrates. Pharmaceutically acceptable excipients are known in the art and may include lubricants, viscosity modifiers, surface active agents, osmotic agents, diluents, and other non-active ingredients of the formulation intended to facilitate handling, stability, dispersibility, wettability, and/or release kinetics of the drug.

In a preferred embodiment, the drug formulation is in a solid or semi-solid form in order to reduce the overall volume of the drug formulation and thereby reduce the size of the device, facilitating implantation. The semi-solid form may be, for example, an emulsion or suspension; a gel or a paste. In many embodiments, the drug formulation desirably includes no or a minimum quantity of excipient for the same reasons of volume/size minimization.

In some embodiments, the drug is a high solubility drug. As used herein, the term "high solubility" refers to a drug having a solubility above about 10 mg/mL water at 37° C. In other embodiments, the drug is a low solubility drug. As used herein, the term "low solubility" refers to a drug having a solubility from about 0.01 mg/mL to about 10 mg/mL water at 37° C. The solubility of the drug may be affected at least in part by its form. For example, a drug in the form of a water soluble salt may have a high solubility, while the same drug in base form may have a low solubility. One example is lidocaine, which has a high solubility of about 680 mg/mL when in the form of a lidocaine hydrochloride monohydrate, a water-soluble salt, but has a low solubility of about 8 mg/mL when in the form of lidocaine base. High solubility drugs may be suited for release due to an osmotic pressure gradient, such as via one or more apertures or passing pores through the device wall, while low solubility drugs may be suited for release via diffusion, such as directly through the device wall or through one or more apertures or passing pores in the device wall. For example, lidocaine base may diffuse directly through a thin silicone wall, while lidocaine hydrochloride may not. Thus, the drug may be formulated to have a high or low solubility depending on the intended release mode. In one embodiment, the drug is formulated to improve its apparent solubility in the implantation environment, such as its apparent solubility in urine within the bladder.

In a particular embodiment, the devices provide pain relief to the patient. A variety of anesthetic agents, analgesic agents, and combinations thereof may be used. In embodiments, the device delivers one or more local anesthetic agents. The local anesthetic agent may be a cocaine analogue. In particular embodiments, the local anesthetic agent is an aminoamide, an aminoester, or combinations thereof. Representative examples of aminoamides or amide-class anesthetics include articaine, bupivacaine, carticaine, cinchocaine, etidocaine, levobupivacaine, lidocaine, mepivacaine, prilocaine, ropivacaine, and trimecaine. Representative examples of aminoesters or ester-class anesthetics include amylocaine, benzocaine, butacaine, chloroprocaine, cocaine, cyclomethycaine, dimethocaine, hexylcaine, larocaine, meprylcaine, metabutoxycaine, orthocaine, piperocaine, procaine, proparacaine, propoxycaine, proxymetacaine, risocaine, and tetracaine. These local anesthetics typically are weak bases and may be formulated as a salt, such as a hydrochloride salt, to render them water-soluble, although the anesthetics also can be used in free base or hydrate form. Other anesthetics, such as lontocaine, also may be used. The drug also can be an antimuscarinic compound that exhibits an anesthetic effect, such as oxybutynin or propiverine. The drug also may include other drugs described herein, alone or in combination with a local anesthetic agent.

In certain embodiments, the analgesic agent includes an opioid. Representative examples of opioid agonists include alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. Other opioid drugs, such as mu, kappa, delta, and nociception opioid receptor agonists, are contemplated.

Representative examples of other suitable pain relieving agents include such agents as salicyl alcohol, phenazopyridine hydrochloride, acetaminophen, acetylsalicylic acid, flufenisal, ibuprofen, indoprofen, indomethacin, naproxen.

In certain embodiments, the drug delivery device is used to treat inflammatory conditions such as interstitial cystitis, radiation cystitis, painful bladder syndrome, prostatitis, urethritis, post-surgical pain, and kidney stones. Non-limiting examples of specific drugs for these conditions include lidocaine, glycosaminoglycans (e.g., chondroitin sulfate, sulodexide), pentosan polysulfate sodium (PPS), dimethyl sulfoxide (DMSO), oxybutynin, mitomycin C, heparin, flavoxate, ketorolac, or a combination thereof. For kidney stones, the drug(s) may be selected to treat pain and/or to promote dissolution of renal stones.

Other non-limiting examples of drugs that may be used in the treatment of IC include nerve growth factor monoclonal antibody (MAB) antagonists, such as Tanezumab, and calcium channel alpha-2-delta modulators, such as PD-299685 or gabepentin. Evidence suggests that the bladder expresses nerve growth factor (NGF) locally, since exogenously delivered NGF into the bladder induces bladder hyperactivity and increases the excitability of dissociated bladder afferent neurons (*Nature Rev Neurosci* 2008; 9:453-66). Accordingly, it would be advantageous to locally deliver a MAB or other agent against NGF using the described delivery devices, significantly reducing the total dose needed for therapeutic efficacy. Evidence also suggests that binding of the alpha-2-delta unit of voltage-sensitive calcium channels, such as with gabapentin, may be effective in the treatment of diseases of neuropathic pain such as fibromyalgia and that there may be common mechanisms between IC and diseases of neuropathic pain (See *Tech Urol.* 2001 March, 7(1):47-49). Accordingly, it would be advantageous to locally deliver a calcium channel alpha-2-delta modulator, such as PD-299685 or gabepentin, using the described delivery devices, minimizing does-related systemic toxicities in the treatment of IC.

Other intravesical cancer treatments include small molecules, such as Apaziquone, adriamycin, AD-32, doxorubicin, doxetaxel, epirubicin, gemcitabine, HTI-286 (hemiastellin analogue), idarubicin, γ-linolenic acid, mitozantrone, meglumine, and thiotepa; large molecules, such as Activated macrophages, activated T cells, EGF-dextran, HPC-doxorubicin, IL-12, IFN-a2b, IFN-γ, α-lactalbumin, p53 adenovector, TNFα; combinations, such as Epirubicin+BCG, IFN+farmarubicin, Doxorubicin+5-FU (oral), BCG+IFN, and Pertussis toxin+cystectomy; activated cells, such as macrophages and T cells; intravesical infusions such as IL-2 and Doxorubicin; chemosensitizers, such as BCG+antifirinolytics (paramethylbenzoic acid or aminocaproic acid) and Doxorubicin+verapimil; diagnostic/imaging agents, such as Hexylaminolevulinate, 5-aminolevulinic acid, Iododexyuridine, HMFG1 Mab+Tc99m; and agents for the management of local toxicity, such as Formaline (hemorrhagic cystitis).

In one particular embodiment, the drug delivery device is used in association with the placement of a ureteral stent, such as to treat pain, urinary urgency or urinary frequency resulting from ureteral stent placement. Non-limiting examples of specific drugs for such treatment include antimuscarinics, α-blockers, narcotics, and phenazopyridine, among others.

The drug delivery device can be used, for example, to treat urinary incontinence, frequency, or urgency, including urge incontinence and neurogenic incontinence, as well as trigonitis. Drugs that may be used include anticholinergic agents, antispasmodic agents, antimuscarinic agents, β-2 agonists, alpha adrenergics, anticonvulsants, norepinephrine uptake inhibitors, serotonin uptake inhibitors, calcium channel blockers, potassium channel openers, and muscle relaxants. Representative examples of suitable drugs for the treatment of incontinence include oxybutynin, S-oxybutylin, emepronium, verapamil, imipramine, flavoxate, atropine, propantheline, tolterodine, rociverine, clenbuterol, darifenacin, terodiline, trospium, hyoscyamin, propiverine, desmopressin, vamicamide, clidinium bromide, dicyclomine HCl, glycopyrrolate aminoalcohol ester, ipratropium bromide, mepenzolate bromide, methscopolamine bromide, scopolamine hydrobromide, iotropium bromide, fesoterodine fumarate, YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide.

In another embodiment, the drug delivery device is used to treat urinary tract cancer, such as bladder cancer and prostate cancer. Drugs that may be used include antiproliferative agents, cytotoxic agents, chemotherapeutic agents, or a combination thereof. Representative examples of drugs which may be suitable for the treatment of urinary tract cancer include Bacillus Calmette Guerin (BCG) vaccine, cisplatin, doxorubicin, valrubicin, gemcitabine, mycobacterial cell wall-DNA complex (MCC), methotrexate, vinblastine, thiotepa, mitomycin, fluorouracil, leuprolide, diethylstilbestrol, estramustine, megestrol acetate, cyproterone, flutamide, a selective estrogen receptor modulators (i.e. a SERM, such as tamoxifen), botulinum toxins, and cyclophosphamide. The drug may be a biologic, and it may comprise a monoclonal antibody, a TNF inhibitor, an antileukin, or the like. The drug also may be an immunomodulator, such as a TLR agonist, including imiquimod or another TLR7 agonist. The drug also may be a kinase inhibitor, such as a fibroblast growth factor receptor-3 (FGFR3)-selective tyrosine kinase inhibitor, a phosphatidylinositol 3 kinase (PI3K) inhibitor, or a mitogen-activated protein kinase (MAPK) inhibitor, among others or combinations thereof. Other examples include celecoxib, erolotinib, gefitinib, paclitaxel, polyphenon E, valrubicin, neocarzinostatin, apaziquone, Belinostat, Ingenol mebutate, Urocidin (MCC), Proxinium (VB 4845), BC 819 (BioCancell Therapeutics), Keyhole limpet haemocyanin, LOR 2040 (Lorus Therapeutics), urocanic acid, OGX 427 (OncoGenex), and SCH 721015 (Schering-Plough). The drug treatment may be coupled with a conventional radiation or surgical therapy targeted to the cancerous tissue.

In still another embodiment, the present intravesical drug delivery device is used to treat infections involving the bladder, the prostate, and the urethra. Antibiotics, antibacterial, antifungal, antiprotozoal, antiseptic, antiviral and other antiinfective agents can be administered for treatment of such infections. Representative examples of drugs for the treatment of infections include mitomycin, ciprofloxacin, norfloxacin, ofloxacin, methanamine, nitrofurantoin, ampicillin, amoxicillin, nafcillin, trimethoprim, sulfonamides trimethoprimsulfamethoxazole, erythromycin, doxycycline, metronidazole, tetracycline, kanamycin, penicillins, cephalosporins, and aminoglycosides.

In other embodiments, the present drug delivery device is used to treat fibrosis of a genitourinary site, such as the bladder or uterus. Representative examples of drugs for the treatment of fibroids include pentoxphylline (xanthine analogue), antiTNF, antiTGF agents, GnRH analogues, exogenous progestins, antiprogestins, selective estrogen receptor modulators, danazol and NSAIDs.

The implantable drug delivery device also may be used to treat neurogenic bladder. Representative examples of drugs for the treatment of neurogenic bladder include analgesics or anaesthetics, such as lidocaine, bupivacaine, mepivacaine, prilocaine, articaine, and ropivacaine; anticholinergics; antimuscarinics such as oxybutynin or propiverine; a vanilloid, such as capsaicin or resiniferatoxin; antimuscarinics such as ones that act on the M3 muscarinic acetylcholine receptor (mAChRs); antispasmodics including $GABA_B$ agonists such as baclofen; botulinum toxins; capsaicins; alpha-adrenergic antagonists; anticonvulsants; serotonin reuptake inhibitors such as amitriptyline; and nerve growth factor antagonists. In various embodiments, the drug may be one that acts on bladder afferents or one that acts on the efferent cholinergic transmission, as described in Reitz et al., *Spinal Cord* 42:267-72 (2004).

The possible drug useful for treatment of neurogenic bladder may be categorized into one of two general types: those for treating spastic neurogenic bladder and those for treating flaccid neurogenic bladder. In one embodiment, the drug is selected from those known for the treatment of incontinence due to neurologic detrusor overactivity and/or low compliant detrusor. Examples of these types of drugs include bladder relaxant drugs (e.g., oxybutynin (antimuscarinic agent with a pronounced muscle relaxant activity and local anesthetic activity), propiverine, impratroprium, tiotropium, trospium, terodiline, tolterodine, propantheline, oxyphencyclimine, flavoxate, and tricyclic antidepressants; drugs for blocking nerves innervating the bladder and urethra (e.g., vanilloids (capsaicin, resiniferatoxin), botulinum-A toxin); or drugs that modulate detrusor contraction strength, micturition reflex, detrusor sphincter dyssynergia (e.g., GABAb agonists (baclofen), benzodiazapines). In another embodiment, the drug is selected from those known for the treatment of incontinence due to neurologic sphincter deficiency. Examples of these drugs include alpha adrenergic agonists, estrogens, beta-adrenergic agonists, tricyclic antidepressants (imipramine, amitriptyline). In still another embodiment, the drug is selected from those known for facilitating bladder emptying (e.g., alpha adrenergic antagonists (phentolamine) or cholinergics). In yet another embodiment, the drug is selected from among anticholinergic drugs (e.g., dicyclomine), calcium channel blockers (e.g., verapamil) tropane alkaloids (e.g., atropine, scopolamine), nociceptin/orphanin FQ, and bethanechol (e.g., m3 muscarinic agonist, choline ester).

The excipient of the drug formulation may be a matrix material, selected to modulate or control the rate of release of the drug from the reservoir. In one embodiment, the matrix material may be a resorbable or non-resorbable polymer. In another embodiment, the excipient comprises a hydrophobic or amphiphilic compound, such as a lipid (e.g., a fatty acids and derivatives, mono-, di- and triglycerides, phospholipids, sphingolipids, cholesterol and steroid derivatives, oils, vitamins and terpenes). The drug formulation may provide a temporally modulated release profile or a more continuous or consistent release profile. Other drugs and excipients may be used for other therapies.

In some embodiments, the drug formulation is in solid form. For example, the drug formulation is formed into solid drug units that are loaded into the drug reservoir portion. Each of the drug units is a solid, discrete object that substantially retains a selectively imparted shape (at the temperature and pressure conditions to which the delivery device normally will be exposed during assembly, storage, and handling before implantation). The drug units may be in the form of tablets, pellets, or beads, although other configurations are possible. For example, FIGS. 1 and 2 illustrate a number of the solid drug units 112 that are suited for implantation loaded into the drug reservoir lumen 108 of the drug delivery device 100.

The drug tablets made by a direct compression tableting process, a molding process, or other processes known in the pharmaceutical arts. The tablets optionally may be coated with one or more materials known in the art for protecting the tablets against destructive exposure to oxygen or humidity during tablet handling, device assembly and storage; for facilitating device loading; for aesthetics; or for facilitating, retarding, or otherwise controlling in vivo dissolution and drug release characteristics. The drug formulation also may be loaded into the drug reservoir in workable form and may cure therein. Thereafter, the solidified drug may be broken along the length of the drug reservoir to form the interstices or breaks that permit device deformation. For example, in embodiments in which the drug formulation is configured to be melted and solidified, the drug formulation can be melted, injected into the drug reservoir in melted form, solidified in the drug reservoir, and broken into pieces in the drug reservoir to accommodate device deformation or movement. The drug formulation also may be extruded with the drug reservoir, may cure within the drug reservoir, and subsequently may be broken along the length of the reservoir to accommodate device deformation.

The drug tablet includes a drug content and may include an excipient content. The drug content includes one or more drugs or active pharmaceutical ingredients (API), while the excipient content includes one or more excipients. The term "excipient" is known in the art, and representative examples of excipients useful in the present drug tablets may include ingredients such as binders, lubricants, glidants, disintegrants, colors, fillers or diluents, coatings and preservatives, as well as other ingredients to facilitate manufacturing, storing, or administering the drug tablet.

In order to maximize the amount of drug that can be stored in and released from a given drug delivery device of a selected (small) size, the drug tablet preferably comprises a high weight fraction of drug or API, with a reduced or low weight fraction of excipients as are required for tablet manufacturing and device assembly and use considerations. For the purposes of this disclosure, terms such as "weight fraction," "weight percentage," and "percentage by weight" with reference to drug, or API, refers to the drug or API in the form employed, such as in salt form, free acid form, free base form, or hydrate form. For example, a drug tablet that has 90% by weight of a drug in salt form may include less than 90% by weight of that drug in free base form.

In one embodiment, the drug tablet is more than 50% by weight drug. In a preferred embodiment, 75% or more of the weight of the drug tablet is drug, with the remainder of the weight comprising excipients, such as lubricants and binders that facilitate making the drug tablet. For the purposes of this disclosure, the term "high weight fraction" with reference to the drug or API means that excipients constitute less than 25 wt %, preferably less than 20 wt %, more preferably less than 15 wt %, and even more preferably less than 10 wt % of the drug tablet. In some cases, the drug content comprises about 75% or more of the weight of the drug tablet. More particularly, the drug content may comprise about 80% or more of the weight of the drug tablet. For example, the drug content may comprise between about 85% and about 99.9% of the weight of the drug tablet. In some embodiments, the excipient content can be omitted completely.

In one embodiment, the drug and excipients are selected and the tablet formulated to be water soluble, so that the drug tablets can be solubilized when the device is located within the vesical, to release the solubilized drug. In a preferred embodiment, the drug tablets are formulated to be sterilizable, either within or outside of the drug delivery device, without substantial or detrimental changes in the chemical or physical composition of the drug tablets. Such drug tablets may be quite different from conventional drug tablets, which typically include active ingredients that constitute less than 50% of the drug tablet content by weight, with the remainder of the drug tablet comprising excipients that are often insoluble and/or may not be suited for conventional sterilization. Furthermore, the present drug tablets may be sized and shaped for use with an implantable drug delivery device. For example, the drug tablets may be "mini-tablets" that are much smaller in size than conventional tablets, which may permit inserting the drug tablets through a lumen such as the urethra into a cavity such as the bladder. An embodiment of a solid drug tablet 112 for intravesical insertion or other in vivo implantation is shown in FIGS. 1-3.

In embodiments in which one or more pharmaceutically acceptable excipients are included, the excipients may facilitate loading the solid drug units in the device. For example, the excipients may increase the lubricity of the drug units so that the drug units can slide with reference to the interior lumen walls of the drug reservoir portion. The excipients also may facilitate forming the therapeutic agent or agents into a solid drug tablet that can be loaded into the drug reservoir portion. The excipients also may affect the kinetics of drug release from the device, such as by increasing or retarding the solubility or dissolution rate of the drug units. In some embodiments, however, the drug release rate is predominately controlled by characteristics of the drug reservoir, such as the tube thickness and permeability to water or urine, while the excipient content of the drug units is primarily selected to permit reliable production of drug units that are solid and include a relatively high weight fraction of drug.

The individual drug units may have essentially any selected shape and dimension that fits within the device. In one embodiment, the drug units are sized and shaped such that the drug reservoir portion is substantially filled by a select number of drug units. Each drug unit may have a cross-sectional shape that substantially corresponds to a cross-sectional shape of the drug reservoir portion. For example, the drug units 112 are substantially cylindrical in shape as shown in FIGS. 1 and 3 for positioning in the substantially cylindrical drug reservoir lumen 108 shown in FIG. 1. Once loaded, the drug units 112 substantially fill the drug reservoir lumen 108, forming the drug reservoir portion 102.

The drug units may have outer dimensions that are about the same as, are slightly less than, or slightly exceed inner dimensions of the drug reservoir portion. In embodiments in which the outer dimensions of the drug units exceed the inner dimensions of the drug reservoir portion, the drug units may be loaded into the drug reservoir portion under a flow of pressurized gas that causes the drug reservoir portion to expand outward so that the drug units travel through it. When the flow of pressurized gas is removed, the drug reservoir portion may return to hold the drug units in selected axial positions. Using larger diameter drug units may increase the payload and thus the amount of drug that can be delivered from a drug delivery device of a given size. For example, the drug unit 112 shown in FIGS. 1-3 has an outer diameter that slightly exceeds an inner diameter of the drug reservoir lumen 108 shown in FIG. 3. Such drug units 112 may be loaded into the lumen 108 under a flow of pressurized gas that radially expands the drug reservoir wall 122 so that the drug units 112 may travel through the drug reservoir lumen 108 in an axial direction, and when the flow of pressurized gas is removed, the wall 122 may return to retain the drug units 112 in selected axial positions along the length of the lumen 108, as shown in FIG. 1. It is noted that the drug units 112 are shown smaller than the lumen 108 merely for the purpose of visually differentiating the two parts. In embodiments in which the outer dimensions of the drug units are smaller than the inner dimensions of the drug reservoir portion, the drug units may have reduced contact with the drug reservoir portion. Therefore, the drug units may be loaded using a flow of pressurized gas at relatively lower pressure, as the flow of pressurized gas may not need to overcome the force of friction.

In embodiments, the drug units are shaped to align in a row when housed in the drug reservoir. Each drug unit has a cross-sectional shape that corresponds to the cross-sectional shape of the drug reservoir, and each drug unit may have end face shapes that correspond to the end faces of adjacent drug units. Thus, once the drug tablets are loaded in the drug reservoir, the line or row of drug tablets may substantially fill the drug reservoir with interstices or breaks formed between adjacent drug units. The interstices or breaks accommodate deformation or movement of the device, such as during deployment, while permitting the individual drug units to retain their solid form. Thus, the drug delivery device may be relatively flexible or deformable despite being loaded with a solid drug, as each drug unit may be permitted to move with reference to adjacent drug units.

An example is shown in FIGS. 1-3, which illustrates the drug unit 112 having circular flat end faces and a cylindrical side wall. Thus, the drug unit 112 can be aligned in a row with other drug units 112 for loading into the cylindrical drug reservoir lumen 108 as shown in FIGS. 1 and 2. When so loaded, the drug units 112 substantially fill the drug reservoir lumen 108, with interstices or breaks 116 formed between them to accommodate deformation or movement. The flat end faces permit piecewise flexibility of the device while limiting the volume or space within the drug reservoir portion that is devoted to the interstices or breaks 116. Thus, the device can be substantially filled with solid drug while retaining its flexibility. Loading the device with a number of drug tablets 112, such as drug tablets that are relatively uniform in size and shape, beneficially permits manufacturing a device that behaves as expected in response to expected forces during and after implantation and exhibits expected drug release characteristics once implanted. That is, the tablet uniformity advantageously enables reproducibility in producing the medical product and thereby generally provides reliable, repeatable drug release characteristics.

In some embodiments, the drug units are relatively tall and slender, unlike conventional drug tablets that tend to be short and squat. The drug units may be tall enough to retain their orientation once loaded in the drug reservoir, with reduced tipping or rolling. On the other hand, the drug units may be short enough to provide enough interstices or breaks so that the device can flex or move along its length. In particular, each drug unit may have a length that exceeds its width, meaning an aspect ratio of height:width that is greater than 1:1. Suitable aspect ratios for the drug units may be in the range of about 3:2 to about 5:2, although other aspect ratios are possible, including aspect ratios that are less than 1:1, like conventional drug tablets. An example is shown in FIG. 1, which illustrates the drug unit 112 with a length that exceeds its diameter.

In embodiments in which the solid drug tablets are designed for insertion or implantation in a lumen or cavity in the body, such as the bladder, via a drug delivery device, such as a device of the type described above with reference to FIGS. 1-3, the drug tablets may be "mini-tablets" that are suitably sized and shaped for insertion through a natural lumen of the body, such as the urethra. For the purpose of this disclosure, the term "mini-tablet" generally indicates a solid drug tablet that is substantially cylindrical in shape, having end faces that are relatively planar or flat and a side face that is substantially cylindrical. An example mini-tablet is shown in FIG. 1. The mini-tablet 112 has a diameter, extending along the end face, in the range of about 1.0 to about 3.2 mm, such as between about 1.5 and about 3.1 mm. The mini-tablet has a length, extending along the side face, in the range of about 1.7 mm to about 4.8 mm, such as between about 2.0 mm and about 4.5 mm. The friability of the tablet may be less than about 2%. Embodiments of solid drug tablets and systems and methods of making the same are further described below with reference to U.S. Patent Applications incorporated by reference herein.

In a preferred embodiment, the drug tablets include lidocaine. A drug delivery device having drug tablets that primarily comprise lidocaine may be wholly deployed in the bladder of a patient in need of treatment for interstitial cystitis, neurogenic bladder, or pain, among others. Other diseases or conditions may also be treated using this device. In other embodiments, other drugs, alone or in combination with lidocaine, may be used to treat interstitial cystitis or other diseases and conditions involving the bladder.

Once the solid drug tablets are formed, the drug tablets may be loaded into the drug delivery device. After the device is loaded, the device preferably is sterilized. The selected sterilization process does not undesirably alter the physical or chemical composition of the solid drug tablets or other components of the device. Examples of suitable sterilization processes include gamma irradiation or ethylene oxide sterilization, although other sterilization processes may be used. For example, gamma irradiation at a strength of about 8 KGy to about 40 KGy, such as about 25 KGy, can be employed.

The drug tablets can be formed using a stable and scalable manufacturing process and are suitable for the intended use. Particularly, the drug tablets are sized and shaped for loading into and efficiently storing the tablets in a linear array in a drug delivery device that can be deployed into the bladder or another cavity, lumen, or tissue site in a patient in a minimally invasive manner.

In addition, the drug tablets can be sterilized before or after loading/assembly into a drug delivery device, and the drug tablets possess a commercially reasonable shelf life. Once implanted, the composition of the drug tablets is appropriate for the intended route of administration, is stable in acidic conditions, and provides pre-selected, reproducible drug release kinetics. For example, the drug tablets may be solubilized in the bladder to continuously release drug at a suitably stable rate drug over an extended period.

Although mini-tablets and other solid drug tablets are described above as having a high weight fraction of drug or API and a low weight fraction of excipients, the solid drug tablets may have any weight fraction of drug, especially in cases in which the tablet includes a drug that is extremely potent, a stabilizing agent, or an agent that increases the solubility of the drug, among others or combinations thereof.

The Retention Frame Portion

The drug delivery device may include a retention frame portion. The retention frame portion is associated with the drug reservoir portion and permits retaining the drug reservoir portion in the body, such as in the bladder. The retention frame portion may include a retention frame that is deformable between a relatively expanded shape and a relatively lower-profile shape. For example, the retention frame may naturally assume the relatively expanded shape, may be manipulated into the relatively lower-profile shape for insertion into the body, and may spontaneously return to the relatively expanded shape upon insertion into the body. The retention frame in the relatively expanded shape may be shaped for retention in a body cavity, and the retention frame in the relatively lower-profile shape may be shaped for insertion into the body through the working channel of a deployment instrument such as a catheter or cystoscope. To achieve such a result, the retention frame may have an elastic limit, modulus, and/or spring constant selected to impede the device from assuming the relatively lower-profile shape once implanted. Such a configuration may limit or prevent accidental expulsion of the device from the body under expected forces. For example, the device may be retained in the bladder during urination or contraction of the detrusor muscle.

In a preferred embodiment, the retention frame includes or consists of an elastic wire. In one embodiment, the elastic wire may comprise a biocompatible shape-memory material or a biodegradable shape memory polymer as described in U.S. Pat. No. 6,160,084 to Langer et al. The elastic wire also may include a relatively low modulus elastomer, which may be relatively less likely to irritate or cause ulcer within the bladder or other implantation site and may be biodegradable so that the device need not be removed. Examples of low modulus elastomers include polyurethane, silicone, styrenic thermoplastic elastomer, and poly(glycerol-sebacate) (PGS). The elastic wire may be coated with a biocompatible polymer, such as a coating formed from one or more of silicone, polyurethane, styrenic thermoplastic elastomer, Silitek, Tecoflex, C-flex, and Percuflex.

For example, in the embodiment shown in FIGS. 1-2, the retention frame 114 is an elastic wire formed from a superelastic alloy, such as nitinol, and surrounded by the wall 124 of the retention frame lumen 110, which forms a protective sheath about the retention frame 114. The wall 124 may be formed from a polymer material, such as silicone. In other embodiments, the retention frame may be an elastic wire formed from a superelastic alloy, such as nitinol, that is covered in a polymer coating such as a silicone sheath and is attached to the drug reservoir portion.

In some embodiments, the retention frame lumen 110 may include the retention frame 114 and a filling material, such as a polymer filling. An example filling material is a silicone adhesive, such as MED3-4213 by Nusil Technology LLC, although other filling materials may be used. The filling material may fill the void in the retention frame lumen 110 about the retention frame 114. For example, the filling material may be poured into the retention frame lumen 110 about the retention frame 114 and may cure therein. The filling material may reduce the tendency of the drug reservoir lumen 108 to stretch along, or twist or rotate about, the retention frame 114, while maintaining the drug reservoir lumen 108 in a selected orientation with reference to the retention frame 114. The filling material is not necessary, however, and may be omitted.

When the retention frame is in the relatively expanded shape, such as the coiled shapes shown in FIG. 1, the device may occupy a space having dimensions suited to impede expulsion from the bladder. When the retention frame is in the relatively lower-profile shape, such as the elongated shapes shown in FIG. 2, the device may occupy an area suited for insertion into the body, such as through the working channel of a deployment instrument. The properties of the elastic wire cause the device to function as a spring, deforming in response to a compressive load but spontaneously returning to its initial shape once the load is removed. The polymer coating may make the outer surface of the retention frame relatively smooth and soft, reducing irritation of the bladder or other implantation site.

A retention frame that assumes a pretzel shape may be relatively resistant to compressive forces. The pretzel shape essentially comprises two sub-circles, each having its own smaller arch and sharing a common larger arch. When the pretzel shape is first compressed, the larger arch absorbs the majority of the compressive force and begins deforming, but with continued compression the smaller arches overlap, and subsequently, all three of the arches resist the compressive force. The resistance to compression of the device as a whole increases once the two sub-circles overlap, impeding collapse and voiding of the device as the bladder contracts during urination.

In embodiments in which the retention frame comprises a shape-memory material, the material used to form the frame may "memorize" and spontaneously assume the relatively expanded shape upon the application of heat to the device, such as when exposed to body temperatures upon entering the bladder.

The retention frame may be in a form having a high enough spring constant to retain the device within a body cavity, such as the bladder. A high modulus material may be used, or a low modulus material. Especially when a low-modulus material is used, the retention frame may have a diameter and/or shape that provide a spring constant without which the frame would significantly deform under the forces of urination. For example, the retention frame may include one or more windings, coils, spirals, or combinations thereof, specifically designed to achieve a desirable spring constant, such as a spring constant in the range of about 3 N/m to about 60 N/m, or more particularly, in the range of about 3.6 N/m to about 3.8 N/m. Such a spring constant may be achieved by one or more of the following techniques: increasing the diameter of the elastic wire used to form the frame, increasing the curvature of one or more windings of the elastic wire, and adding additional windings to the elastic wire. The windings, coils, or spirals of the frame may have a number of configurations. For example, the frame may be in a curl configuration comprising one or more loops, curls or sub-circles. The ends of the elastic wire may be adapted to avoid tissue irritation and scarring, such as by being soft, blunt, inwardly directed, joined together, or a combination thereof.

Figure 5:
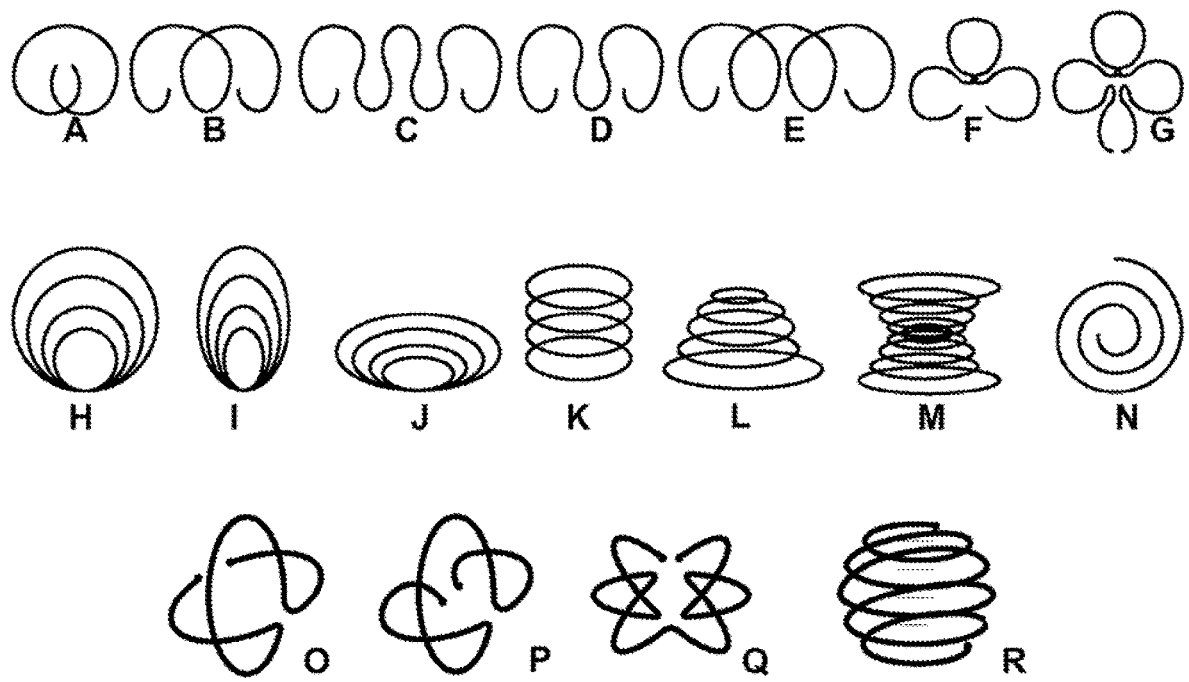
FIG. 5 illustrates examples of shapes for a retention frame of a drug delivery device.

Examples are shown in FIG. 5. The retention frame may have a two-dimensional structure that is confined to a plane, a three-dimensional structure, such as a structure that occupies the interior of a spheroid, or some combination thereof. In particular, Examples A through G illustrate frames comprising one or more loops, curls, or sub-circles, connected either linearly or radially, turning in the same or in alternating directions, and overlapping or not overlapping. Examples H through N illustrate frames comprising one or more circles or ovals arranged in a two-dimensional or a three-dimensional configuration, the circles or ovals either closed or opened, having the same or different sizes, overlapping or not overlapping, and joined together at one or more connecting points. The retention frame portion also may be a three-dimensional structure that is shaped to occupy or wind about a spheroid-shaped space, such as a spherical space, a space having a prorate spheroid shape, or a space having an oblate spheroid shape. Examples O through R illustrate retention frame portions that are shaped to occupy or wind about a spherical space, with each retention frame portion shown above a representation of the frame in a sphere. The retention frame portion may generally take the shape of two intersecting circles lying in different planes as shown in Example O, two intersecting circles lying in different planes with inwardly curled ends as shown in Example P, three intersecting circles lying in different planes as shown in Example Q, or a spherical spiral as shown in Example R. In each of these examples, the retention frame portion can be stretched to the linear shape for deployment through a deployment instrument. The retention frame portion may wind about or through the spherical space, or other spheroid-shaped space, in a variety of other manners. One or both of the retention frame and retention housing may be omitted, in which case the retention portion may be components of the drug portion itself, which may assume or may be deformed into a retention shape, or the retention portion may be an anchor associated with the drug portion.

Examples of alternative configurations are described in the U.S. patent applications incorporated by reference herein.

Other Device Features

The drug reservoir portion can include a coating or a sheath, which may be substantially impermeable to water or relatively less permeable to water than the drug reservoir portion to reduce or alter the osmotic or diffusive surface area of the device body. Thus, the release rate can be independently controlled or targeted with reduced adjustment of desired device characteristics, such as size, shape, material, permeability, volume, drug payload, flexibility, and spring constant, among others. To achieve the release rate, the coating or sheath may cover all or any portion of the device body, and the coating or sheath may be relatively uniform or may vary in thickness, size, shape, position, location, orientation, and materials, among others and combinations thereof. Further, multiple coatings or sheaths may be provided along different portions of the device body, about the same drug reservoir or different drug reservoirs housing the same or different drug formulations. In cases in which the drug reservoir portion is formed from silicone tubing, for example, a coating may be formed from parylene, while a sheath may be formed from a polymer such as polyurethane or curable silicone, or another biocompatible coating or sheath material known in the art. In some embodiments, the coating or sheath may be positioned on the tube between the end and the orifice so that water permeating through the tube adjacent to the end can drive through the portion of the tube covered by the sheath and out of the orifice, reducing or avoiding isolation or stagnation of the drug under the sheath. Coatings and sheaths, and equations for selecting such designs, are described in U.S. Patent Publication No. 2009/0149833.

In one embodiment, the device includes at least one radio-opaque portion or structure to facilitate detection or viewing (e.g., by X-ray imaging or fluoroscopy) of the device by a medical practitioner as part of the implantation or retrieval procedure. In one embodiment, the tube is constructed of a material that includes a radio-opaque filler material, such as barium sulfate or another radio-opaque material known in the art. Some tubing may be made radio-opaque by blending radio-opaque fillers, such as barium sulfate or another suitable material, during the processing of the tubing. The radio-opaque material also may be associated with the retention frame. For example, a platinum wire may be wound about ends of the elastic wire and covered in smoothening material. Ultrasound imaging may be used. Fluoroscopy may be the preferred method during deployment/retrieval of the non-erodible device by providing accurate real-time imaging of the position and orientation of the device to the practitioner performing the procedure.

In one embodiment, the body of the implantable drug delivery device further includes at least one retrieval feature, such as a structure that facilitates removal of the device from the body cavity, for example for removal of a non-resorbable device body following release of the drug formulation.

One example of a retrieval feature is a string, formed of a biocompatible material. The string may be attached to a mid-portion or an end-portion of the drug delivery device. In some embodiments, the string is sized to extend along the urethra from the bladder to the exterior of the body, in which case a proximal end of the string may be positioned outside of the body once the device is positioned in the bladder. The string also may be shorter in size, so that once the device is positioned in the bladder, the proximal end of the string is positioned in the urethra in a location that is reachable by a physician. In either case, the device may be removed from the bladder by engaging the string to pull the device through the urethra. In such embodiments, the diameter of the string may be sized to fit comfortably in the urethra during the period of implantation. In other embodiments, the string is sized to be wholly implanted in the bladder with the device, in which case the string facilitates locating and grasping the device within the bladder using a removal instrument positioned in the urethra, such as a cystoscope or catheter.

In embodiments in which the string is attached to a mid-portion of the drug delivery device, the device may fold upon itself as it enters the removal instrument or the urethra. Folding at the mid-portion may be facilitated once the drug delivery device has released at least a portion of the drug or is empty. In embodiments in which the string is attached to an end-portion of the drug delivery device, the device may move into the deployment shape as it enters the removal instrument or the urethra. Thus, the deployment shape also may be considered a retrieval shape in such embodiments.

Embodiments of retrieval features are described in U.S. Patent Publication No. 2007/0202151 A1. In these and in other embodiments, the device may be retrieved using conventional endoscopic grasping instruments, such as alligator forceps, three or four-pronged optical graspers. For example, if the device has an O-shaped or coiled portion, the removal of the device can be facilitated by those grasping instruments.

Combination of the Components

Figure 6:
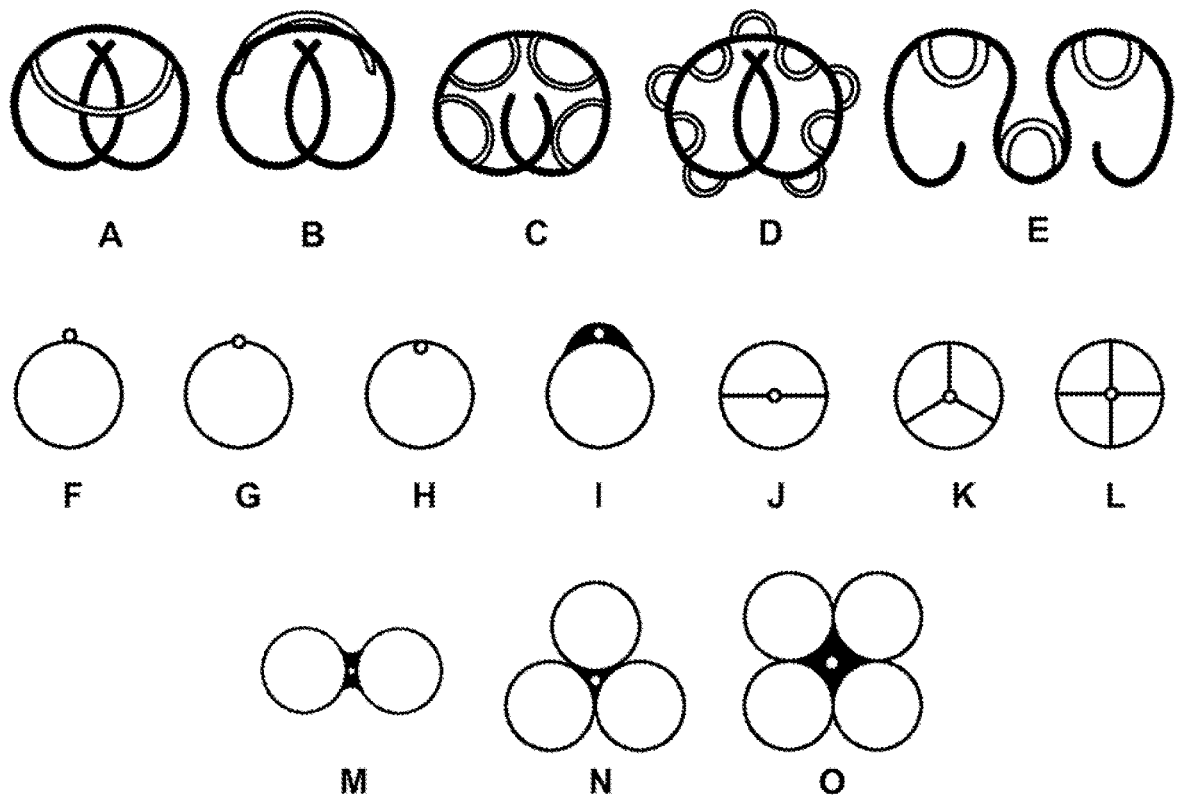
FIG. 6 illustrates examples of configurations for drug delivery devices having at least one drug delivery portion and a retention frame portion.

The drug reservoir portion and the retention frame portion are associated with each other to form the drug delivery device. A variety of different associations are envisioned. For example, the drug reservoir portion and the retention frame portion may be at least partially aligned. In other words, the drug reservoir portion may extend along a portion or the entire length of the retention frame portion, substantially parallel or coincident with the retention frame portion. An example of such an embodiment is shown in FIGS. 1-3. FIG. 6 also illustrates several alternative embodiments in cross-section. As shown in Examples F, G, H, and I, the retention frame wire may extend along either an exterior surface of the drug reservoir wall, along an interior surface of the drug reservoir wall, through the drug reservoir wall, or within a reinforced area inside or outside of the wall. As shown in Examples J, K, and L, the elastic wire may also be positioned within the interior of the tube supported by a web, which may partition the tube into multiple compartments. The web may be perforated or otherwise non-continuous so that the compartments are in communication with each other, or the web may be relatively continuous such that the compartments are segregated from each other to form different reservoirs that may be suited for holding different drug formulations. The web may be formed from the same material as the tube, or from a material having a different permeability to water or urine, depending on the embodiment. As shown in Examples M, N, and O, the elastic wire may be associated with multiple tubes, extending along or between the tubes. The elastic wire may be embedded in a reinforcement area that joins together multiple discrete tubes. The tubes may hold the same or different drug formulations and also may be formed from the same or different materials of construction, such as materials that differ in permeability to urine or other aqueous or bodily fluids.

In other embodiments, the drug reservoir portion may be attached to only a portion of the retention frame. The drug reservoir portion may have first and second end portions that are attached to a portion of the retention frame. The end portions of the drug reservoir may terminate at the retention frame, the end portions may overlap the retention frame, or a combination thereof. The drug reservoir portion may be oriented with reference to the retention frame portion such that the drug reservoir portion lies within the perimeter of the retention frame portion, beyond the perimeter of the retention frame portion, or a combination thereof. Additionally, a number of drug reservoir portions may be associated with a single retention frame portion. Examples A through E of FIG. 6 illustrate such embodiments.

In other embodiments, the drug reservoir portion and the retention frame portion may be the same component in some embodiments. In such cases, the device may comprise a tube formed in a configuration having a sufficient spring constant to retain the device in the body, as described above. Also, the drug reservoir portion may be wrapped around the retention frame portion, one or any number of times.

The embodiments described herein may be combined and varied to produce other drug delivery devices that fall within the scope of the present disclosure. For example, the drug reservoir portion may be attached to any portion of the retention frame portion in any manner. Multiple drug reservoir portions may be provided, a single drug reservoir portion may be partitioned, or a combination thereof, which may facilitate delivering multiple different drugs into the body, delivering different forms of drugs into the body, delivering drugs at varying rates into the body, or a combination thereof.

Furthermore, when the device is in the retention shape, the retention frame portion may have any orientation with reference to the drug reservoir portion, laying either inside, outside, above, or below the drug reservoir portion or moving with reference to the drug reservoir portion as the device moves through the implantation site. For example, the device 100 includes a retention frame portion that lies inside the perimeter of the drug reservoir portion. In other embodiments, the device includes a retention frame portion that lies below the drug reservoir portion (such that the retention frame portion would not be visible in FIG. 1). A particular orientation between the two portions can be maintained by filling the retention frame portion with a filling material, such as a silicone adhesive, after the retention frame is loaded. The filling material may cure or solidify to prevent movement of one portion with reference to the other. Other means of maintaining the orientation of the retention frame portion with reference to the drug reservoir portion also can be used.

The aperture may be positioned inside the perimeter of the device, outside of the perimeter of the device, or an upper or lower plane of the device. For example, the device 100 includes an aperture 118 located on an outside perimeter of the device, but in other embodiments the aperture is located on an upper plane of the device. An aperture positioned on the inside perimeter or on the upper or lower plane of the device advantageously may be less likely to become positioned directly adjacent to a portion of the implantation site, such as the bladder wall, delivering a large quantity of drug to one particular location. The aperture also may be formed in a groove or indent defined between the walls of the drug reservoir portion and the retention frame portions, so that the walls serve as bumpers that impede the aperture from becoming positioned directly adjacent to the implantation site. For example, the aperture 118 of the device 100 could instead be formed in a groove or indent between the walls 122 and 124.

For ease of manufacturing, the aperture may be formed through the wall of the drug reservoir portion on an opposite side from the retention frame portion, as shown in FIG. 3. When the aperture is positioned opposite from the retention frame portion, it may be desirable to secure the retention frame portion below the device as described above, so that the aperture becomes positioned above the device, reducing the risk of the aperture becoming positioned on the outside perimeter of the device. However, other configurations are possible.

It should be noted that the device 400 shown in FIG. 4 has a slightly different shape and configuration than the device 100 shown in FIG. 1. For example, the ends of the device 400 are relatively straighter than the ends of device 100. The straighter ends may result because the retention frame of the device 400 has relatively straight end portions, while the retention frame of the device 100 has relatively curved end portions. A retention frame with relatively straight end portions may be less likely to puncture the walls of the device body during drug loading and thereafter, reducing the risk of device failure after implantation. However, either retention frame shape can be used.

In the embodiment shown in FIG. 1, for example, the drug delivery device 100 is suited for delivering a drug into the bladder. The drug reservoir lumen 108 may have an inner diameter of about 1.3 to about 3.3 mm, such as about 1.5 to about 3.1 mm, an outer diameter of about 1.7 to about 3.7 mm, such as about 1.9 to about 3.4 mm, and a length of about 12 to 21 cm, such as about 14 to 16 cm. The drug reservoir lumen 108 may hold about 10 to 100 cylindrical drug tablets, such mini-tablets. The mini-tablets may each having a diameter of about 1.0 to about 3.3 mm, such as about 1.5 to about 3.1 mm, and a length of about 1.5 to about 4.7 mm, such as about 2.0 to about 4.5 mm. Such mini-tablets may have a lidocaine payload of about 3.0 to about 40.0 mg. One particular example of a mini-tablet may have a diameter of about 1.52 mm, a length of about 2.0 to 2.2 mm, and a mass of about 4.0 to 4.5 mg lidocaine. Another particular example of a mini-tablet may have a diameter of about 2.16 mm, a length of about 2.9 to 3.2 mm, and a mass of about 11.7 to 13.1 mg lidocaine. Yet another particular example of a mini-tablet may have a diameter of about 2.64 mm, a length of about 3.5 to 3.9 mm, and a mass of about 21.3 to 23.7 mg lidocaine. Still another particular example of a mini-tablet may have a diameter of about 3.05 mm, a length of about 4.1 to 4.5 mm, and a mass of about 32.7 to 36.9 mg lidocaine. However, other diameters, lengths, and masses can be used.

Within these ranges, the device may be designed to deliver between about 150 mg and 1000 mg of lidocaine to the bladder, such as about 200 mg, about 400 mg, about 600 mg, or about 800 mg of lidocaine. For example, a smaller payload may be delivered from a smaller device or from a device loaded with fewer tablets, the remainder of the space in the device being loaded with a spacer or filling material.

The foregoing specific configurations are merely possibilities of the type of devices that may be created by a person skilled in the art upon reading the present disclosure. For example, in some embodiments the drug reservoir portion may be omitted completely, and the retention frame portion may be associated with another component for retention in the body, such as the bladder. Examples of other components include diagnostic equipment, test materials, and small electronic devices, such as cameras and sensors, among others.

II. Method of Making the Device

An embodiment of a method of making an implantable drug delivery device may include forming a drug delivery device, forming a number of drug tablets, and loading the drug tablets into the drug delivery device.

In embodiments, forming the drug delivery device may include one or more of the following sub-steps: forming a device body, forming a retention frame, associating the device body with the retention frame, and forming one or more apertures in the device body.

Forming the device body may include forming a flexible body having walls that define a drug reservoir lumen and a retention frame lumen. For example, the device body may be formed by extruding or molding a polymer, such as silicone. In particular, forming the device body may include integrally forming two tubes or walls that are substantially aligned and adjoined along a longitudinal edge. Alternatively, the two lumens may be separately formed and attached to each other, such as with an adhesive. Other methods of forming the device body also may be employed.

Forming a retention frame may include forming an elastic wire from, for example, a superelastic alloy or shape-memory material and "programming" the elastic wire to naturally assume a relatively expanded shape. Heat treatment may be used to program the elastic wire to assume the expanded shape. For example, the retention frame may be formed by forming the elastic wire into a pretzel shape and heat treating the elastic wire at a temperature over 500° C. for a period over five minutes. In embodiments in which the retention frame comprises a low modulus elastomer, the step of forming the vesical retention frame may comprising forming one or more windings, coils, loops or spirals in the frame so that the frame functions as a spring. For example, the retention frame may be formed by extrusion, liquid injection molding, transfer molding, or insert molding, among others.

Associating the device body with the retention frame may comprise inserting the retention frame into the retention frame lumen of the device body. In some embodiments, a distal end of the retention frame is blunted or is covered in a smooth ball of increased cross section during insertion of the retention frame into the lumen. The ball may facilitate driving the retention frame through the retention frame lumen without puncturing the wall of the device body. Also in some embodiments, the device body may be slightly compressed between two surfaces during the insertion of the retention frame. Compressing the device body elongates the opening into the retention frame lumen, facilitating loading.

In some embodiments, associating the device body with the retention frame further includes filling the retention frame lumen with a filling material after the retention frame is loaded. The filling material occupies the remainder of the lumen not occupied by the retention frame, reducing the ability of the device body to stretch along, or twist or rotate about, the retention frame. For example, silicone or another polymer may be injected or poured into the retention frame lumen and may cure therein. In other embodiments, associating the device body with the retention frame portion may comprise integrally forming the two portions together, such as by overmolding the device body about the retention frame.

Forming one or more apertures in the device body may include laser drilling or mechanically punching one or more holes in the device body. The apertures also may be formed simultaneously with the device body, such as by molding with an indenter as described in U.S. Pat. No. 6,808,522 to Richards et al.

The drug tablets made by a direct compression tableting process, a molding process, or other processes known in the pharmaceutical arts. Suitable drug tablet forming methods are described in U.S. patent applications incorporated by reference herein.

The drug tablets may be loaded into the drug delivery device by positioning one or more drug tablets upstream of the drug delivery device adjacent to its entry and driving the drug tablets into the drug delivery device with a flow of pressurized gas. Suitable drug tablet loading methods and systems are described in U.S. patent applications incorporated by reference herein. Other drug tablet loading methods can be used.

Some steps or sub-steps of the method of making an implantable drug delivery device may be performed in other orders or simultaneously. For example, the retention frame may be associated with the device body either before or after the drug units are loaded into the device body. Similarly, the apertures may be formed in the device body either before or after the drug tablets are loaded.

In embodiments, the method of making an implantable drug delivery device may further include partitioning the drug reservoir lumen into multiple discrete drug reservoirs, such as by positioning one or more partition structures within the drug reservoir lumen in an alternating fashion with the loading of the drug tablets. In embodiments, the method may further include sealing the drug tablets in the device body. The method may also include associating one or more release controlling structures with the drug reservoir lumen, such as a sheath or coating placed over at least a portion of the surface of the device body to control the rate of release of the drug or a degradable membrane positioned over or in one or more of the apertures to control the initial time of release of the drug therethrough.

III. Use and Applications of the Device

The device may be implanted in a body cavity or lumen, and subsequently may release one or more drugs for the treatment of one or more conditions, locally to one or more tissues at the deployment site and/or regionally to other tissues distal from the deployment site. The release may be controlled over an extended period. Thereafter, the device may be removed, resorbed, excreted, or some combination thereof.

Figure 7:
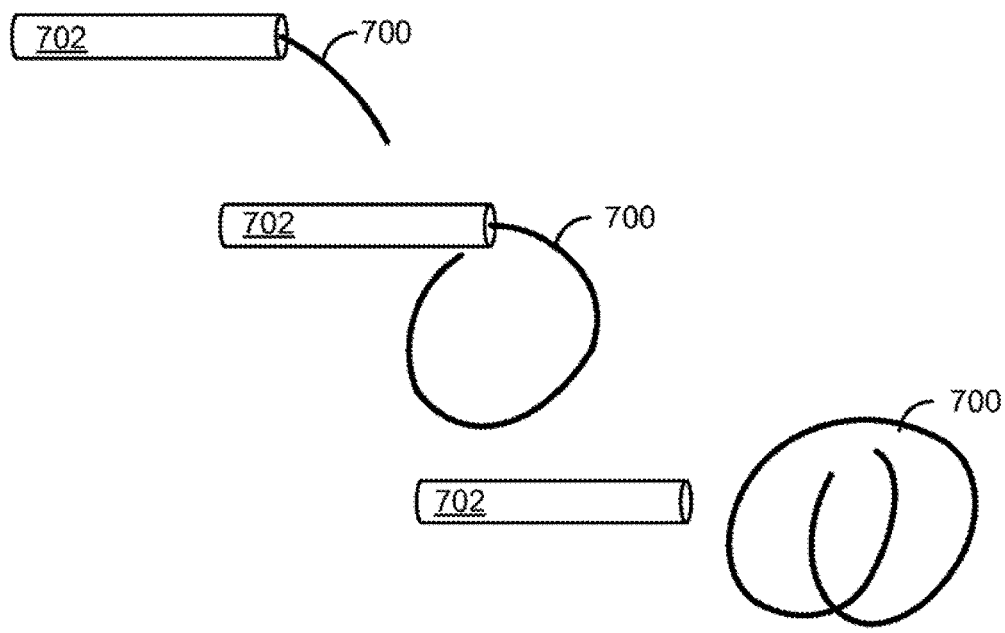
FIG. 7 illustrates a method of implanting a drug delivery device.

In one example, the device is implanted by passing the drug delivery device through a deployment instrument and releasing the device from the deployment instrument into the body. In cases in which the device is deployed into a body cavity such as the bladder, the device assumes a retention shape, such as an expanded or higher profile shape, once the device emerges from the deployment instrument into the cavity. An example is illustrated in FIG. 7, which shows the device 700 assuming a retention shape as the device exits a deployment instrument 702. The deployment instrument 702 may be any suitable lumen device, such as a catheter, urethral catheter, or cystoscope. These terms are used interchangeably herein, unless otherwise expressly indicated. The deployment instrument 702 may be a commercially available device or a device specially adapted for the present drug delivery devices.

Once implanted, the device may release the drug. The device may provide extended, continuous, intermittent, or periodic release of a desired quantity of drug over a desired, predetermined time period. In embodiments, the device can deliver the desired dose of drug over an extended period, such as 12 hours, 24 hours, 5 days, 7 days, 10 days, 14 days, or 20, 25, 30, 45, 60, or 90 days, or more. The rate of delivery and dosage of the drug can be selected depending upon the drug being delivered and the disease or condition being treated.

In embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

Subsequently, the device may be retrieved from the body, such as in cases in which the device is non-resorbable or otherwise needs to be removed. Retrieval devices for this purpose are known in the art or can be specially produced. The device also may be completely or partially bioresorbable, such that retrieval is unnecessary, as either the entire device is resorbed or the device sufficiently degrades for expulsion from the bladder during urination. The device may not be retrieved or resorbed until some of the drug, or preferably most or all of the drug, has been released. If needed, a new drug-loaded device may subsequently be implanted, during the same procedure as the retrieval or at a later time.

Figure 8:
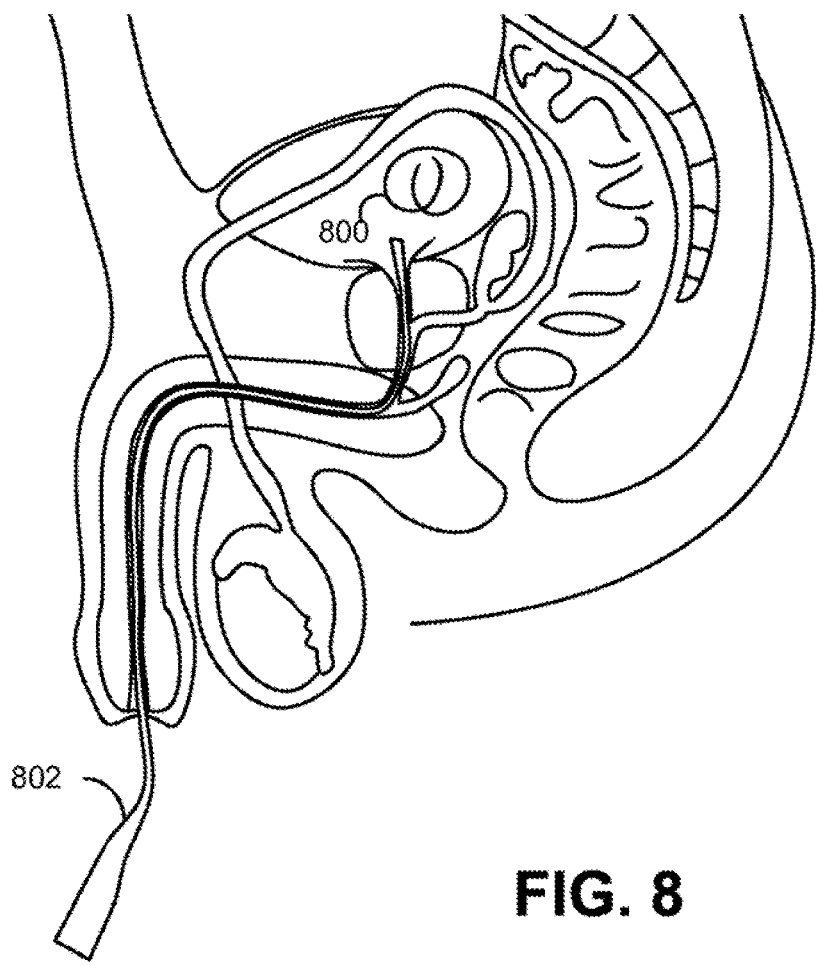
FIG. 8 is a sagittal view of a male patient, illustrating a drug delivery device exiting a deployment instrument into a bladder of the patient.

FIG. 8 illustrates the implantation of a device 800 into the bladder, wherein the adult male anatomy is shown by way of example. A deployment instrument 802 may be inserted through the urethra to the bladder, and the device 800 may be passed through the deployment instrument 802, driven by a stylet or flow of lubricant or other fluid, for example, until the device 800 exits into the bladder. Thus, the device is implanted into the bladder of a male or female human patient in need of treatment, either adult or child.

The device may be deployed into the bladder of a patient in an independent procedure or in conjunction with another urological or other procedure or surgery, either before, during, or after the other procedure. The device may release one or more drugs that are delivered to local and/or regional tissues for therapy or prophylaxis, either peri-operatively, post-operatively, or both.

In one embodiment, the implantable device, with a self-contained drug payload, is deployed wholly within the bladder to provide local, sustained delivery of at least one drug locally to the bladder in an effective amount. Following in vivo deployment of the device, at least a portion of the payload of drug is released from the device substantially continually over an extended period, to the urothelium and possibly to nearby tissues, in an amount effective to provide treatment or to improve bladder function in the patient. In a preferred embodiment, the device resides in the bladder releasing the drug over a predetermined period, such as two weeks, three weeks, four weeks, a month, or more.

In such cases, the device may be used to treat interstitial cystitis, radiation cystitis, pelvic pain, overactive bladder syndrome, bladder cancer, neurogenic bladder, neuropathic or non-neuropathic bladder-sphincter dysfunction, infection, post-surgical pain or other diseases, disorders, and conditions treated with drugs delivered to the bladder. The device may deliver drugs that improve bladder function, such as bladder capacity, compliance, and/or frequency of uninhibited contractions, that reduce pain and discomfort in the bladder or other nearby areas, or that have other effects, or combinations thereof. The bladder-deployed device also may deliver a therapeutically effective amount of one or more drugs to other genitourinary sites within the body, such as other locations within urological or reproductive systems of the body, including one or both of the kidneys, the urethra, one or both of the ureters, the penis, the testes, one or both of the seminal vesicles, one or both of the vas deferens, one or both of the ejaculatory ducts, the prostate, the vagina, the uterus, one or both of the ovaries, or one or both of the fallopian tubes, among others or combinations thereof. For example, the intravesical drug delivery device may be used in the treatment of kidney stones or fibrosis, erectile dysfunction, among other diseases, disorders, and conditions.

In some embodiments, the intravesical drug delivery device is deployed into the bladder of a patient for regional drug delivery to one or more nearby genitourinary sites. The device may release drug locally to the bladder and regionally to other sites near the bladder. Such delivery may provide an alternative to systemic administration, which may entail undesirable side effects or result in insufficient bioavailability of the drug.

In one embodiment, the intravesical drug delivery device is implanted into a bladder to locally deliver a local anesthetic agent for management of pain arising from any source, such as a disease or disorder in genitourinary tissues, or pain stemming from any bladder procedure, such as surgery, catheterization, ablation, medical device implantation, or stone or foreign object removal, among others.

In some cases, the device can release a local anesthetic agent into the bladder for regional delivery to nearby sites, as described in Example 9 below. The local anesthetic agent can facilitate the management of nearby pain arising from any source. For example, the device may release a local anesthetic agent into the bladder for the purpose of treating post-operative pain in sites apart from the bladder. In one example, the drug delivery device implanted in the bladder may release a drug to treat post-operative pain associated with the passage of a medical device into or through a ureter. The device also may achieve regional delivery of drugs other than local anesthetic agents, and the device through regional delivery may treat conditions other than post-operative pain.

In one particular embodiment, a device having a payload of lidocaine may be delivered to the bladder, and lidocaine may be continuously released from the device over an extended period. In one embodiment, local delivery of lidocaine to the urothelium of the bladder is provided from the presently disclosed devices which have been deployed into the bladder in a manner which achieves a sustained level of lidocaine above the concentration that could be obtained for an extended period via instillation, yet without the high initial peak observed with instillation and without significant systemic concentrations. Thereby, a small payload may be implanted, reducing the risk of systemic effects in the event of device failure. Implanting lidocaine in solid form permits further reducing the size of the device to reduce bladder irritation and patient discomfort. The lidocaine may be delivered without regard to the pH of the urine. In one embodiment, the device may have two payloads of lidocaine that are released at different times. The first payload may be adapted for relatively quick release, while the second payload may be adapted for more continuous release. For example, the first payload may be in liquid form or may be housed in a relatively fast-acting osmotic pump, such as a silicone tube having a relatively thinner wall, while the second payload may be solid form or may be housed in an osmotic pump that experiences an initial delay or induction time before releasing, such as a silicone tube having a relatively thicker wall. Thus, the method may continuously release lidocaine into the bladder during an initial, acute phase and during a maintenance phase. Such a method may compensate for an initial induction time of the device.

Methods of Use of the Tolerable and Unnoticeable Device

Examples 4, 5, 6, and 7 describe in vivo studies that show that the drug delivery devices described herein upon being deployed in the bladder of a human or dog may be surprisingly well tolerated, and in the case of the humans, more unexpectedly, may be essentially unnoticeable in the bladder. That is, a device described herein cannot be felt by the patient. Based on this tolerability discovery, certain new methods of treatment of human patients may be provided.

This attribute of the present devices enables the physicians to select drug therapies for indications where just being tolerable does not outweigh the benefit gained by the delivery of drug. The highly tolerable (unnoticeable) device described herein can extend local drug therapy to the bladder beyond those patients with high unmet medical needs, to include those who may want to consider therapeutic alternatives to current strategies. For example, patients with refractory over active bladder disease (failing one or more anticholinergics agents due to lack of efficacy or side effects) would likely tolerate a system for local delivery of drug that might have less than favorable tolerability profile. A device that cannot be noticed in the bladder could, however, extend treatment to patients with less severe disease and be directly competitive with first-line oral anticholinergics use. Another example is for the treatment of patients with chronic urinary tract infections. Standard of care is daily oral antibiotic use for months at a time to suppress bladder infections. The highly tolerable device described here may supplant chronic oral therapy and provide a superior therapeutic option due to less of a concern with patient compliance (forgetting a dose) which can lead to bacterial resistance. Additional examples where bladder tolerability is a primary concern include interstitial cystitis, radiation cystitis, painful bladder syndrome, prostatitis, urethritis, urinary incontinence, urge incontinence, neurogenic incontinence, trigonitis, spastic neurogenic bladder, flaccid neurogenic bladder, bladder infection, prostate infection, urethra infection, perioperative pain associated with urological procedure or surgery, and postoperative pain associated with urological procedure or surgery.

In one embodiment, the method includes selecting a patient in need of treatment in the bladder where tolerability of the treatment is a primary concern; deploying a drug delivery device into the patient's bladder; and releasing a drug from the deployed drug delivery device, wherein the deployed drug delivery device is unusually well tolerated by the patient. As used herein, the phrase "patient in need of treatment in the bladder where tolerability of the treatment is a primary concern" means that at least one alternative drug therapy, e.g., an oral drug therapy, is available for administration to the patient for the purpose of meeting the patient's need for treatment, which alternative therapy does not include deployment of a drug delivery device into the patient's bladder. Selection of such a patient is made before it is known whether the alternative oral drug therapy would be effective in the particular patient. Tolerability is not a primary concern where the patient is in need of treatment of a life-threatening condition or where no oral drug therapy is available and effective for the patient. Tolerability is primary concern where the patient is in need of treatment of a chronic condition where alternative first line drug treatments exist and are available.

In one embodiment, a method of treatment of a human patient is provided which includes (i) selecting a patient in need of treatment in the bladder where tolerability of the treatment is a primary concern; (ii) deploying a drug delivery device into the patient's bladder through the patient's urethra; and (iii) releasing a drug into the bladder from the deployed drug delivery device over a treatment period, which may last several days or weeks. In a preferred embodiment, the patient cannot feel the deployed device within his or her bladder during at least a majority of the treatment period.

The present invention may be further understood with reference to the following non-limiting examples.

Example 1: A Drug Delivery Device

Figure 9:
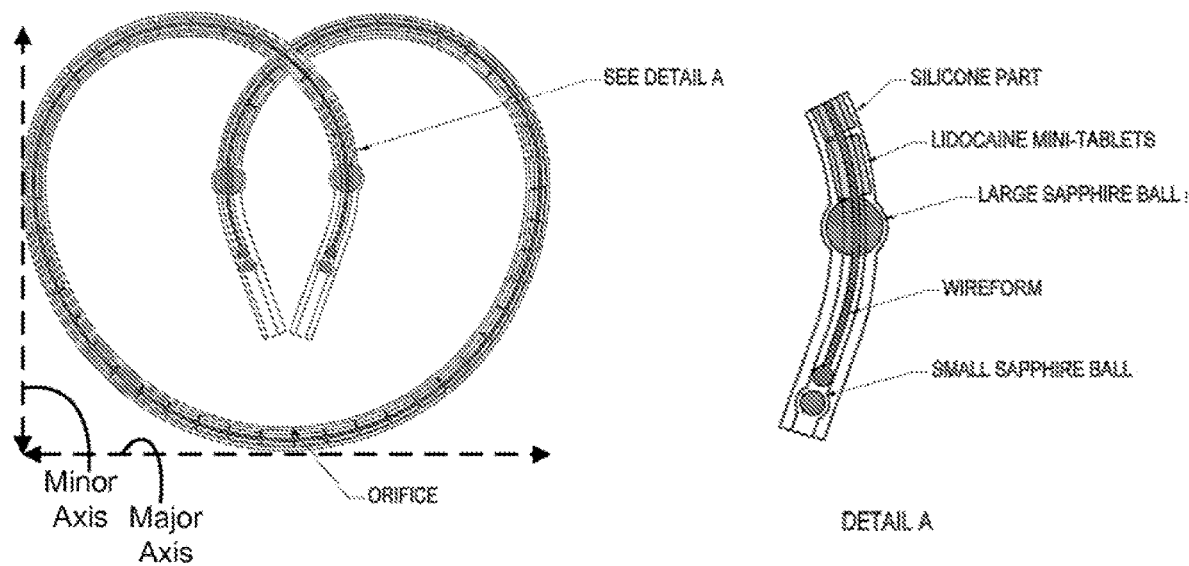
FIG. 9 is a detailed cross-sectional plan view of an embodiment of a drug delivery device.

A drug delivery device, schematically illustrated in FIG. 9, was created in accordance with the description provided above. The device included a silicone body having two lumens. A larger lumen was loaded with solid tablets of lidocaine hydrochloride for a total drug payload of about 275 mg. A smaller lumen was loaded with a nitinol wireform having a diameter of about 0.23 mm. The nitinol wireform generally retained the device in the illustrated rest shape. In the rest shape, the device generally rested in a plane defined by a minor or short axis, which was an axis of symmetry for the device, and a major or long axis, which was generally perpendicular to the minor or short axis. A width or maximum dimension of the device along the major axis was approximately 35 mm, and a height or maximum dimension of the device along the minor axis was approximately 30 mm. A thickness of the device, in a direction perpendicular to the rest plane, was approximately 2.6 mm. When uncoiled, the device had a length of about 17 cm. The density of the device when loaded with tablets and dry was approximately 1.15 g/cm$^3$.

Example 2: A Placebo Device

A placebo device also was fabricated. The placebo device was identical to the device described above with reference to in Example 1 except that the device did not contain any drug tablets in its larger lumen. Therefore, the placebo device had the same parameters as the device of Example 1, except that the placebo device had a density of about 0.62 g/cm$^3$.

Example 3: Another Drug Delivery Device

Figure 10:
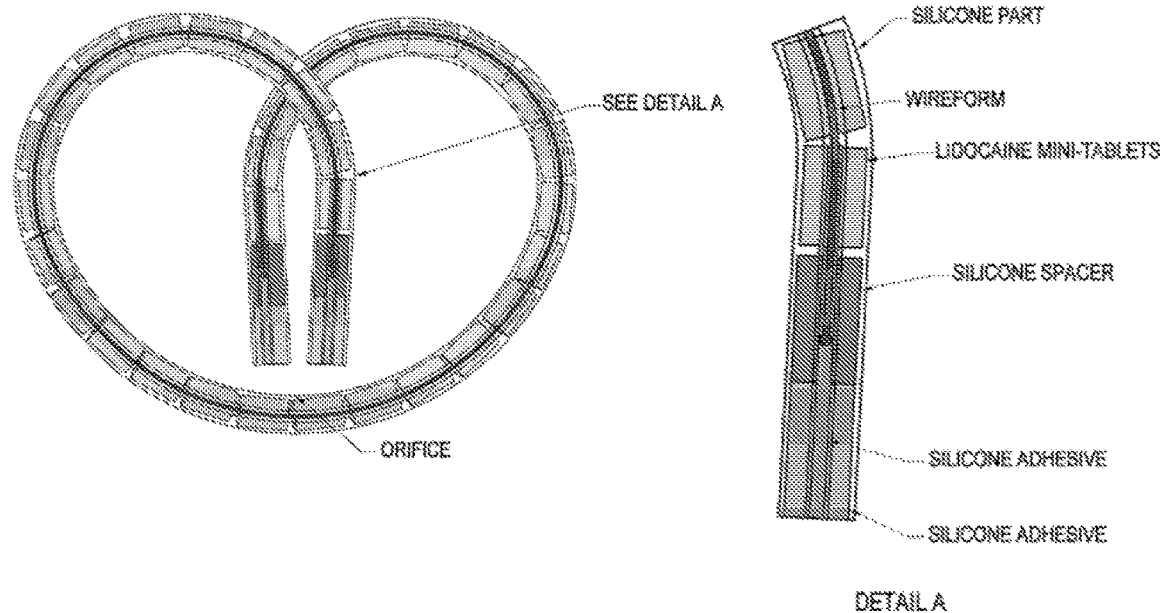
FIG. 10 is a detailed cross-sectional plan view of another embodiment of a drug delivery device.

Another drug delivery device, schematically illustrated in FIG. 10, was created in accordance with the description provided above. The device included a silicone body having two lumens. A larger lumen was loaded with solid tablets of lidocaine hydrochloride for a total drug payload of about 895 mg. A smaller lumen was loaded with a nitinol wireform having a diameter of about 0.28 mm. The nitinol wireform generally retained the device in the illustrated rest shape. In the rest shape, the device generally rested in a plane defined by a minor or short axis, which was an axis of symmetry for the device, and a major or long axis, which was generally perpendicular to the minor or short axis. A width or maximum dimension of the device along the major axis was approximately 45 mm, and a height or maximum dimension of the device along the minor axis was approximately 35 mm. A thickness of the device, in a direction perpendicular to the rest plane, was approximately 3.75 mm. When uncoiled, the device had a length of about 17 cm. The density of the device when loaded with tablets and dry was approximately 1.20 g/cm$^3$.

Example 4: First Tolerability Study

A Phase 1 study (TAR-100-101) was performed to assess subject tolerance of a drug delivery device in accordance with the present disclosure. Ten healthy, adult, female human volunteer subjects participated in the study. The test devices were substantially similar to the placebo device described above with reference to Example 2. Seven subjects received a test device. The devices were inserted into and retrieved from the bladder via cystoscopy. The devices were inserted for fourteen days and thereafter were removed. Three subjects were subjected to a sham procedure of cystoscopy only, during which no device was implanted in the subject or removed.

Subject-reported symptoms were captured via a Subject Tolerability Assessment (STA) visual analogue scale (VAS). The STA VAS consisted of a 100 mm horizontal line with the word "Typical" at the left end and the word "Not Typical" at the right end. Subjects were instructed to complete the STA VAS by marking the spot on the line that described their urinary voiding behavior within the last 24 hours and by marking the spot on the line that described the sensation in their bladder within the last 24 hours. Additionally, subjects were given the option to record any comments regarding their answers to the above questions. The STA was collected starting pre-insertion on Study Day 1 as a baseline and on all subsequent Study Days.

With reference to sensation in the bladder, the experiences of those subjects who received the test device were largely similar to the experiences of those subjects who underwent the sham procedure. With reference to urinary voiding behavior, the experiences of those subjects who underwent who received the test device also were largely similar to the experiences of those subjects who underwent the sham procedure. No Serious Adverse Events were observed in this study. The study showed that the test device was well tolerated.

Example 5: Second Tolerability Study

An animal study was conducted in dog using test devices substantially in accordance with the device described above with reference to Example 1. Four large mixed breed hounds were employed in the study. A test device was implanted in each dog for 14 days. The test devices were well tolerated over the 14-day period without any significant clinical observations, such as change in weight, eating habits, or voiding behavior. The study showed that the test device was well tolerated in dog.

Example 6: Third Tolerability Study

Another animal study was conducted in dog using test devices substantially in accordance with the device described above with reference to Example 1. Nine female, mixed breed hounds were employed in the study. A test device was placed in the bladder of each hound by cystoscopy. On day 14 after placement, the test device was removed and a second test device of the same type was placed for another 14 days. All test devices were retained over the 14-day periods. All test devices placed in the first treatment period were identified in the bladder and removed by cystoscopy after 14 days. All test devices placed in the second treatment period were identified in the bladder and removed by cystoscopy or necropsy after 14 days. No test devices were voided prematurely. The test devices were well tolerated in female mixed breed hound dogs for 14 days. There were no test-device-related changes in clinical observations, body weights, food consumption, ophthalmological exams, electrocardiograms, and hematology, coagulation, and clinical chemistry parameters. There was no evidence of local or systemic toxicity.

Example 7: Fourth Tolerability Study

Another animal study was conducted in dog using test devices substantially in accordance with the device described above with reference to Example 3. Seven female, mixed breed hounds were employed in the study. A test device was placed in the bladder of some of the hounds via cystoscopy, while other hounds were subjected to a sham cystoscopy procedure that did not place a device in the bladder. On day 14 after placement, the test device was removed and a second test device of the same type was placed for another 14 days, or a second sham procedure was performed for the sham group. All test devices were retained in female mixed breed hound dogs for 14 days. All test devices placed in the first treatment period were identified in the bladder and removed by cystoscopy after 14 days. All test devices placed in the second treatment period were identified in the bladder and removed by cystoscopy or necropsy after 14 days. No test devices were voided prematurely. The test devices were well tolerated in female mixed breed hound dogs for 14 days. There were no test device related changes in clinical observations, body weights, food consumption, ophthalmological exams, electrocardiograms, and hematology, coagulation, and clinical chemistry parameters. There was no evidence of local or systemic toxicity.

Example 8: Resistance to Compression for Various Devices

Compression tests were performed on various devices to analyze the compression behavior of the devices when exposed to compressive forces. Five different devices were subjected to the compression tests, and the results of the tests are summarized in FIGS. 11 and 12. The tested devices included a nitinol wire having a diameter of about 0.23 mm (shown in FIGS. 11 and 12 as the wire form of 0.009 inch thickness), a nitinol wire having a diameter of about 0.28 mm thickness (shown in FIGS. 11 and 12 as the wire form of 0.011 inch thickness), a drug-loaded device that was substantially similar to the device described above in Example 1 (shown in FIGS. 11 and 12 as Device A), a placebo device that was substantially similar to the device described above in Example 2 (shown in FIGS. 11 and 12 as the Placebo device for Device A), and a drug-loaded device that was substantially similar to the device described above in Example 3 (shown in FIGS. 11 and 12 as Device B). Both the placebo device and the loaded devices were gamma-irradiated with the dose of 25 kGy.

Figure 11:
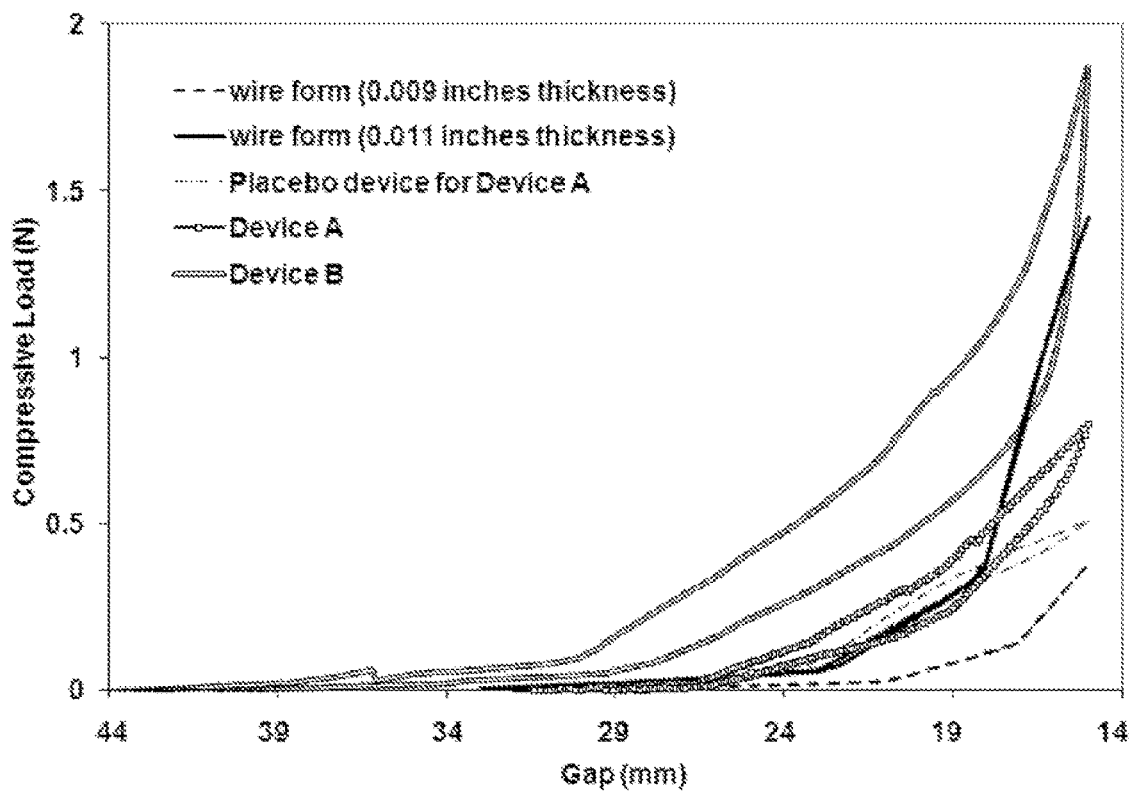
FIG. 11 is a graph compression along the long axis for various devices, meaning compression that tends to change the shape of the device along its longer axis as a compressive force is applied to the device along its longer axis.
Figure 12:
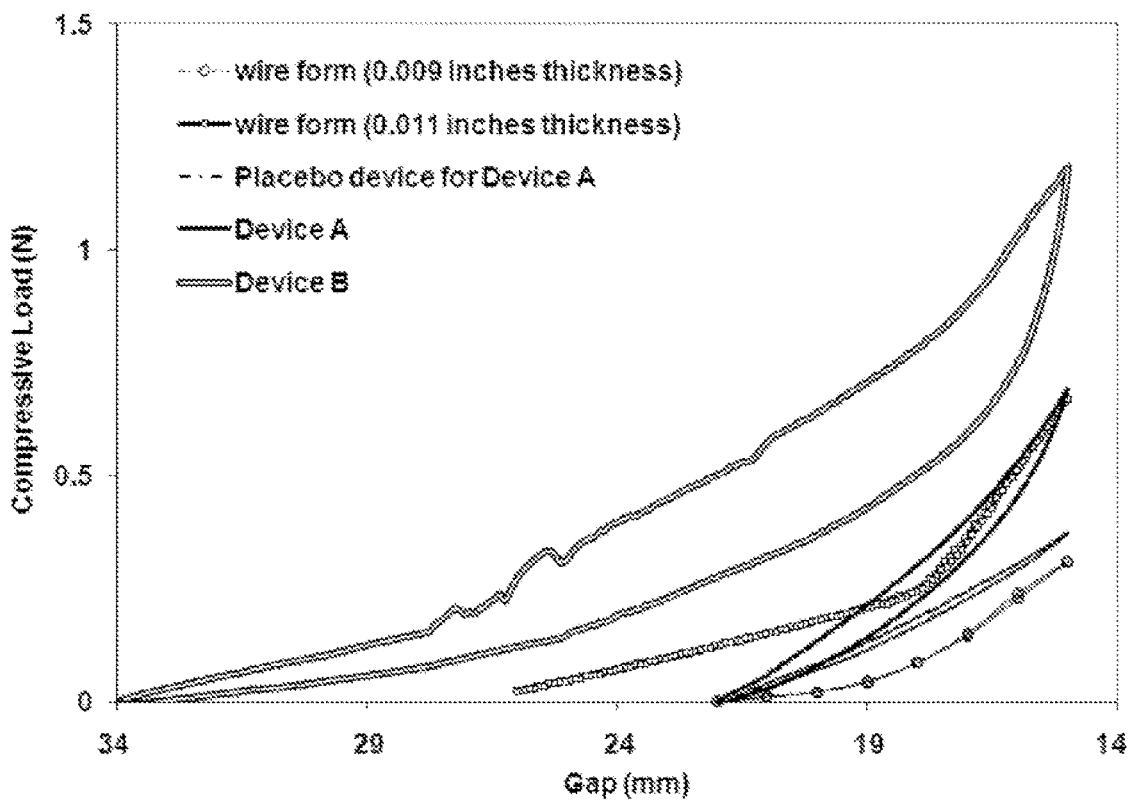
FIG. 12 is a graph that illustrates compression along the short axis for various devices, meaning compression that tends to change the shape of the device along its shorter axis as a compressive force is applied to the device along its shorter axis.

The devices were subjected to compression tests. Data was collected for one compression cycle. FIG. 11 illustrates compression along the long axis, meaning compression that tends to change the shape of the device along its longer axis as a compressive force is applied to the device along its longer axis, while FIG. 12 illustrates compression along the short axis, meaning compression that tends to change the shape of the device along its shorter axis as a compressive force is applied to the device along its shorter axis.

For the tests, the compression rate was set to 30 mm/min, and the compressive load was recorded while the gap between two compression platens varied. The devices were compressed until the gap between the two compression platens was 15 mm. The results of the tests are plotted in FIGS. 11 and 12. For each device on each graph, the upper curve was obtained during compression and the lower curve was obtained during relaxation The force exerted by the loaded device of Example 1 during compression to a gap distance of 30 mm was less than 0.01 N in both the long and short axis. The force exerted by the placebo device of Example 2 during compression was similarly less than 0.01 N in both the long and short axis, at the same gap distance. Finally, the force exerted by the loaded device of Example 3 during compression to a gap distance of 30 mm was 0.1 N in both the long and short axis.

Example 9: Regional Drug Delivery

A study was conducted in rabbit to investigate the biodistribution of lidocaine delivered from a drug delivery device implanted in the bladder. Four rabbits were used in the experiment. Each rabbit had a test device implanted in its bladder. The test devices had the general shape and configuration shown in FIG. 6. Two of the rabbits received a test device housing 2 mg of lidocaine and were sacrificed after three days, while the other two rabbits received a test device housing 4 mg of lidocaine and were sacrificed after six days.

The test device housing 2 mg of lidocaine included a nitinol wire form and a drug-loaded silicone tube. The wire form had a thickness of 0.2286 mm and was covered with silicone tubing having an inner diameter of 0.508 mm and an outer diameter of about 0.9398 mm. The drug-loaded silicone tube had an inner diameter of about 0.3048 mm and an outer diameter of about 0.635 mm. The tube was loaded with about 2 mg of lidocaine and was sealed at both ends. A hole having a diameter of about 50 µm was formed about a middle of the tube, and the tube was attached to the nitinol wire form, spanning its major width. Overall, the device was about 30 mm wide along its major axis, about 25 mm wide about its minor axis, and about 1 mm thick.

The test device housing 4 mg of lidocaine was substantially the same in configuration as the test device housing 2 mg of lidocaine, except that the silicone tube had an inner diameter of about 0.508 mm and an outer diameter of 0.9398 mm, and the tube was loaded with about 4 mg of lidocaine.

Tissue samples were taken from each of the rabbits, particular from the bladder, the ureters, the kidney, the heart, the spinal cord, and the penile urethra of each rabbit. The ureter samples were taken from the distal portion of each ureter. The kidney samples were taken from the cortex and medulla of one lobe. The heart samples were taken from the myocardium at the apex. The spinal cord samples were taken via laminectomy from L5 to L7. The samples were subjected to enzyme-linked immunosorbent assay (ELISA) to detect lidocaine and its metabolites.

Figure 13:
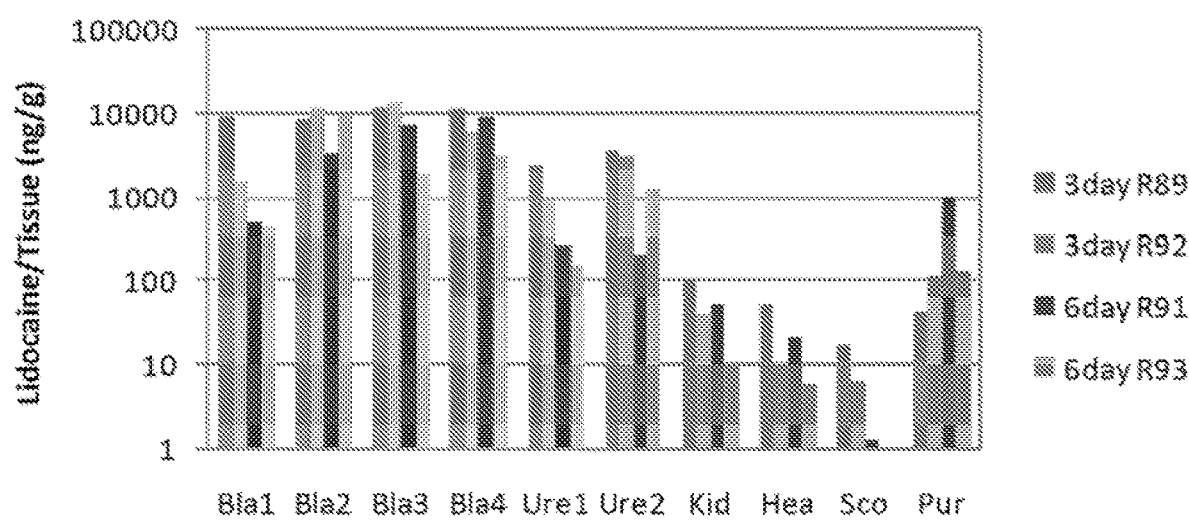
FIG. 13 is a biodistribution graph for a study conducted in vivo in rabbit, illustrating the tissue concentration of lidocaine at various sampled locations.

FIG. 13 is a biodistribution graph shows the lidocaine/tissue concentration for each of the rabbits at each of the sampled locations. For each sampled location, FIG. 13 illustrates the concentration detected in the first three-day rabbit on the far left, the second three-day rabbit on the middle left, the first six-day rabbit on the middle right, and the second six-day rabbit on the far right. As shown, the devices implanted in the bladder delivered higher concentrations of lidocaine to the bladder tissue and nearby genitourinary sites, such as the kidneys, ureters, and penile urethra; whereas lower concentrations of lidocaine were delivered to further sites such as the heart and the spinal cord. For the two rabbits that were euthanized after six days, the cerebrospinal fluid also was sampled just prior to euthanasia by spinal cord puncture at L7. Lidocaine was not detected in the cerebrospinal fluid of either rabbit.

Example 10: Resistance to Hydrodynamic Forces During Urination

A voiding experiment was conducted to empirically determine whether devices of the shape described above with reference to FIG. 1 could resist hydrodynamic forces during urination. Any portion of the device that is located right above the internal urethral orifice during urination will undergo hydrodynamic force. It was thought that each device would resist the hydrodynamic forces associated with urination if its associated wire had a sufficient stiffness.

Two devices were tested. One was substantially similar to the device described above with reference to Example 1 and the other was substantially similar to the device described above with reference to Example 2. The first device was calculated to have a bending spring constant of about 890 N/m, and the second device was calculated to have a bending spring constant of about 2000 N/m. The term bending spring constant generally connotes the spring constant related to bending perpendicular to the wire axis. Using linear analysis, a correlation between the force and displacement was obtained.

The experiment was conducted in a vertical PVC tube with an open latex balloon at the bottom end, secured in place by a cap with a drilled hole. Voiding was simulated by filling the PVC tube with soapy water to a pre-determined height then allowing the water to flow freely through the latex balloon neck. The neck was confined to a diameter of about 6 mm, controlled by the drilled hole in the cap, as the diameter of the internal urethral orifice in women is about 6 mm. It was found that both devices that were modeled and tested indeed resisted the hydrodynamic forces during the voiding experiment.

Another observation was that the devices would not experience the most severe hydrodynamic forces during voiding if the devices were floating at the beginning of the process, when the most severe hydrodynamic forces occur. The floating device approached the opening towards the end of voiding, when the fluid velocities and flow rates of water exiting the orifice were lower. It was noted that a device could avoid voiding potential voiding simply by not being located near the opening when urination began, such as by having a density slightly lower. Such a device would still need a minimum spring constant to resist the low hydrodynamic forces at the end of urination, but the requirements could be significantly reduced.

It was also observed the device could be voided from the system if one of its extremities or ends was located directly above the opening as voiding occurred. This risk may be reduced by designing the device to have no ends or so that its extremities does not approach the urethral opening when the device is either at rest or exposed to drag due to the by hydrodynamic forces.

Thus, a device that may be retained in a bladder during urination if portions of the device that could be located near the urethral opening during urination are able to resist maximum hydrodynamic forces during urination; if the device has no extremities, or if the extremities are positioned such that they cannot be located adjacent to the urethral opening; or if the device that is less dense than urine and thereby does not experience the maximum hydrodynamic forces during urination. The device also may need to have a resistance to bending.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A drug delivery device for deployment within the bladder of a human patient which is well tolerated by the patient, comprising:
   an elongated elastic body comprising a first end, an opposed second end, an annular portion disposed between the first end and the second end, and a drug reservoir lumen defined at least in part by the annular portion; and
   a drug formulation loaded in the drug reservoir lumen, the drug formulation comprising a drug,
   wherein the device has a retention shape having (i) dimensions that provide intravesical mobility and that prevent voiding of the device through the urethra, and (ii) dimensions, buoyancy, or both, that exclude the device from entering the orifices of the ureters, wherein the retention shape has a maximum dimension in any dimension of 6 cm or less when in an uncompressed state, and wherein the device exerts a maximum acting force less than 1 N when the device is compressed from the retention shape to a shape having a maximum dimension in any dimension of 3 cm.

2. The device of claim 1, further comprising a retention frame portion which comprises an elastic wire and biases the device into the retention shape, wherein the elongated elastic body and the retention frame portion are longitudinally aligned and coupled to one another along their lengths.

3. The device of claim 1, wherein the device exerts a maximum acting force less than 1 N when the device is compressed from the retention shape to a shape having a maximum dimension in any dimension of 1.5 cm.

4. The device of claim 1, wherein the device is configured to provide controlled release of the drug by diffusion through a wall of the elastic body.

5. The device of claim 1, wherein the device is configured to provide controlled release of the drug through an aperture in the elastic body, driven at least in part by an osmotic pressure in the drug reservoir lumen.

6. The device of claim 1, wherein the retention shape has a maximum dimension in any direction that is less than 5 cm when in an uncompressed state.

7. The device of claim 1, wherein the retention shape has a maximum dimension in any direction that is less than 4 cm when in an uncompressed state.

8. The device of claim 1, wherein the elastic body is elastically deformable to take a low-profile shape having an outer diameter in one direction that is less than about 4 mm.

9. The device of claim 1, wherein the drug formulation is in a solid or semi-solid form.

10. The device of claim 9, wherein a cross-sectional shape of the drug formulation corresponds to a cross-sectional shape of the drug reservoir lumen.

11. The device of claim 9, wherein the drug formulation has a circular cross-sectional shape, and wherein the drug reservoir lumen has a circular cross-sectional shape.

12. The device of claim 1, wherein the drug formulation is in a liquid form.

13. The device of claim 1, wherein the retention shape is coiled.

14. The device of claim 1, further comprising a retention frame portion, wherein the retention frame portion comprises an elastic wire.

15. The device of claim 1, wherein the elastic body comprises silicone, polyurethane, or a combination thereof.

16. A method of treatment of a human patient comprising:
    selecting a patient in need of treatment in the bladder where tolerability of the treatment is a primary concern;
    deploying the drug delivery device of claim 1 into the patient's bladder through the patient's urethra; and
    controllably releasing the drug into the bladder from the deployed drug delivery device over a treatment period.

17. The method of claim 16, wherein the patient cannot feel the deployed device within his or her bladder during at least a majority of the treatment period.

18. The method of claim 16, wherein the selected patient is indicated to be in need of treatment for overactive bladder, painful bladder syndrome, and/or interstitial cystitis.

19. The method of claim 16, wherein the selected patient is indicated to be in need of treatment for an infection of the bladder, prostate, or urethra.

20. The method of claim 16, wherein the selected patient is indicated to be in need of treatment for neurogenic bladder.

21. The method of claim 16, wherein the selected patient is indicated to be in need of treatment for prostatitis or urethritis.

22. The method of claim 16, wherein the selected patient is indicated to be in need of treatment for perioperative or postoperative pain associated with a urological surgery on the patient.

23. The method of claim 16, wherein the drug comprises lidocaine or another anesthetic agent.

24. The device of claim 1, wherein the drug formulation is able to move within the drug reservoir lumen.

25. The device of claim 1, wherein the drug reservoir lumen has a cylindrical shape.

26. The device of claim 1, wherein the drug reservoir lumen comprises a first end and an opposed second end, and wherein the first end and the second end of the drug reservoir lumen are sealed.

27. The device of claim 1, wherein the drug reservoir lumen is substantially filled by the drug formulation.

28. A drug delivery device for deployment in and mobility within the bladder of a human patient, comprising:
    an elongated elastic body comprising a first end, an opposed second end, an annular portion disposed between the first end and the second end, and a drug reservoir lumen defined at least in part by the annular portion; and
    a drug formulation disposed in the drug reservoir lumen, the drug formulation comprising a drug,
    wherein the device is elastically deformable between (i) a deployment shape for passage of the device through a urethra of the patient and (ii) a retention shape for preventing voiding of the device through the urethra, the retention shape having a maximum dimension in any dimension of 6 cm or less when in an uncompressed state, and
    wherein the device exerts a maximum acting force less than 1 N when the device is compressed from the retention shape to a shape having a maximum dimension in any dimension of 3 cm.

29. The device of claim 28, wherein the retention shape comprises an overlapping coil.

30. The device of claim 29, further comprising a retention frame portion which comprises an elastic wire and biases the device into the retention shape.

31. The device of claim 30, wherein the elongated elastic body and the retention frame portion are longitudinally aligned and coupled to one another along their lengths.

32. The device of claim 30, wherein the elastic wire comprises a superelastic alloy.

33. The device of claim 29, wherein the device is configured to provide controlled release of the drug through a single aperture in the device.

34. The device of claim 29, wherein the device has an overall exterior shape which is curved and a cross-sectional shape which is rounded.

35. The device of claim 34, wherein the first end and the second end lie within an interior region of the device when the device is uncompressed in the retention shape.

36. The device of claim 29, wherein the retention shape has a maximum dimension in any direction that is less than 4 cm.

37. The device of claim 29, wherein the retention shape has a maximum dimension in any direction that is less than 3 cm.

38. A device for deployment in and mobility within the bladder of a human patient, comprising:

a retention frame portion which comprises an elastic wire and biases the device into a retention shape; and an electronic component attached to the retention frame portion, wherein the device is elastically deformable between (i) a deployment shape for passage of the device through a urethra of the patient and (ii) the retention shape which prevents voiding of the device through the urethra, the retention shape having a maximum dimension in any dimension of 6 cm or less when in an uncompressed state, and wherein the device exerts a maximum acting force less than 1 N when the device is compressed from the retention shape to a shape having a maximum dimension in any dimension of 3 cm.

39. The device of claim 38, wherein the electronic component comprises a camera or a sensor.

* * * * *